(12) United States Patent
Zhang et al.

(10) Patent No.: US 9,315,492 B2
(45) Date of Patent: Apr. 19, 2016

(54) HETEROCYCLIC GROUP CONTAINED AMINO-METHANOL DERIVATIVE, AND SALT, SYNTHETIC METHOD AND USE THEREOF

(71) Applicant: BEIJING FORELAND BIOPHARMA CO., LTD., Beijing (CN)

(72) Inventors: Xingmin Zhang, Beijing (CN); Ensi Wang, Beijing (CN); Jing Guo, Beijing (CN); Shengxiu Niu, Beijing (CN); Zhuolin Dai, Beijing (CN); Nan Zheng, Beijing (CN); Liping Ji, Beijing (CN); Zhenfang Wang, Beijing (CN); Tie Liang, Beijing (CN)

(73) Assignee: Beijing Foreland Biopharma Co., Ltd. (CN)

( * ) Notice: Subject to any disclaimer, the term of this patent is extended or adjusted under 35 U.S.C. 154(b) by 0 days.

(21) Appl. No.: 14/563,342

(22) Filed: Dec. 8, 2014

(65) Prior Publication Data

US 2015/0094337 A1 Apr. 2, 2015

Related U.S. Application Data

(60) Provisional application No. PCT/CN2012/076642, filed on Jun. 8, 2012.

(30) Foreign Application Priority Data

Jun. 7, 2012 (CN) .......................... 2012 1 0186211

(51) Int. Cl.
| | |
|---|---|
| *C07D 271/10* | (2006.01) |
| *C07D 271/107* | (2006.01) |
| *C07D 413/04* | (2006.01) |
| *C07D 271/06* | (2006.01) |
| *C07D 249/06* | (2006.01) |

(52) U.S. Cl.
CPC ............ *C07D 413/04* (2013.01); *C07D 249/06* (2013.01); *C07D 271/06* (2013.01); *C07D 271/107* (2013.01)

(58) Field of Classification Search
CPC .......................... C07D 271/10; C07D 271/107
USPC .................................. 548/143, 145; 514/364
See application file for complete search history.

(56) References Cited

U.S. PATENT DOCUMENTS 8,907,098 B2 * 12/2014 Stieber et al. ................. 546/209

FOREIGN PATENT DOCUMENTS

| CN | 101768086 A | 7/2010 |
|---|---|---|
| CN | 102250035 A | 11/2011 |
| CN | 102816128 A | 12/2012 |
| WO | 2010078711 A1 | 7/2010 |

OTHER PUBLICATIONS

Extended European Search Report issued on EP Application No. 12878273.7 on Sep. 24, 2015.
Kotha et al., "The Dlels-Adler Approach for the Synthesis of Tetralin-Based a-Amino Acid Derivatives and their Modificaiton by the Suzuki-Miyaura Cross-Coupling Reaction," Synthesis (2004) 4:558-567.

* cited by examiner

*Primary Examiner* — Patricia L Morris
(74) *Attorney, Agent, or Firm* — Fox Rothschild LLP; Jianming Jimmy Hao; Robert N. Henrie, II

(57) ABSTRACT

The present invention provides a heterocyclic group contained amino-methanol derivative, and salt, a preparation method and use thereof, and belongs to the medical field. The heterocyclic group contained amino-methanol derivative and the salt thereof of the present invention are used for preparing medicines for immune suppression and for the treatment of organ transplant rejection, or medicines for treating immune mediated inflammatory diseases, such as multiple sclerosis, systemic lupus erythematosus and rheumatoid arthritis.

4 Claims, 1 Drawing Sheet

HETEROCYCLIC GROUP CONTAINED AMINO-METHANOL DERIVATIVE, AND SALT, SYNTHETIC METHOD AND USE THEREOF

TECHNICAL FIELD

The invention belongs to medical field, particularly relates to the treatment of organ transplant rejections and immune mediated inflammatory diseases, such as multiple sclerosis, systemic lupus erythematosus and rheumatoid arthritis.

BACKGROUND

The immune system is a self-defensive structure mainly consisting of lymphatic organs (thymus glands, lymph nodes, spleen, tonsils), lymphatic tissues within other organs, lymphocytes throughout the body, antigen presenting cell, and the like. The immune system also includes other leucocytes in blood, and plasma cells and mast cells in connective tissues. The key components of the immune system are lymphocytes, which endue the immune system with the capability of recognition and memory. The lymphocytes travel throughout the body via blood and lymph, migrating from one lymphatic organ or tissue to another lymphatic organ or tissue, and connecting the lymphatic organs or tissues scattered throughout the body to form a functional entirety. T cells and B cells are the most important immunocytes in human bodies. The normal functioning of each component of the immune system provides the guarantee for the relative stability of the body immune functions, and any deficiencies or hyperactions of the component would cause damage to the body.

The components of immune system reach the whole body widely and complicatedly, particularly with the continuous production, circulation, and regeneration of the immune cells and immune molecules. The immune system possesses a great recognizability, which can precisely detect a foreign substance and distinguish it from human's own healthy tissue in order to maintain body's relative stability. Simultaneously, the immune system can accept, transfer, enlarge, depot, and memorize the related immune information, and provide positive or negative responses and regulate the responsibility to the immune information. However, the malfunctions of the immune system are disadvantageous to human body: human's abnormal recognizability easily results in allergy phenomenon, or causes iterative infections conversely; the abnormal stabilizing ability may induce the immune system to give responses to self-cells, which gives rise to autoimmune diseases.

Immunosuppressive agent is a type of new medicine category, which developed from the foundation of the research on neoplasm-chemotherapy, organ transplantation, immunopathology, and clinical immunology, etc. It possesses immunosuppressive effects which inhibits abnormal immune responses, and is generally used in the therapy of organ transplant rejection and autoimmune diseases.

Cyclophosphamide (CTX) was firstly applied to clinical practice, which was discovered to be hydroxylated by hepatocyte microsomes to generate the alkylated metabolite behaving potent and lasting immune functions. It is utilized as an immunosuppressive agent in the treatment of nephritic syndrome, systemic lupus erythematosus, and rheumatoid arthritis and so on by means of killing the immune cells and influencing every phase of the immunologic processes. But it is restricted because of the relatively obvious side effects.

Glucocorticoid is the most commonly used immunosuppressive agent in clinic nowadays, which can inhibit body's immune responses by inhibiting the phagocytic functions of macrophages, reducing the production of an auto-antibody against an auto-antigen. It is generally used for treating acute inflammation, allergy, organ transplant rejection, and some autoimmune diseases, etc.

Azathioprine is an immunosuppressive agent, which inhibits T cells and B cells. Azathioprine has been an effective drug for preventing organ transplant rejection for years, and is also used for various autoimmune diseases.

Cyclosporine A (CsA) is a cytokine synthesis inhibitor, which inhibits gene transcription of T cells cytokine, interrupts T cells production, and interferes activation of T cells. It belongs to an inhibitor of T cells activation at early phase, which interrupts T cells activations at phase G0/G1 (G0, G1 and S are different phases of a cell cycle). Since 1980s, CsA has been successively applied to various organ and tissue transplantations, and achieved abroad successes, which opened a new era for organ transplantations.

FK506 is another kind of binder subsequent to the development of CsA, which can prevent various transplant rejections, especially is useful in liver transplantation. FK506 has immunosuppressive effect 10~100 times stronger than CsA, and has lower acute or chronic rejection rate, lower infection rate, lower dosage of hormone, and less adverse reaction than CsA. FK506 can reverse acute rejection and is expected to replace CsA to be the first choice as an immunosuppressive agent after an organ transplant.

Rapamycin (RPM), firstly used for anti-transplant rejection, can effectively prevent rejection reaction. Rapamycin is able to decrease the acute rejection rate in combination with other drugs. It can specifically inhibit the phosphorylation and activity of protein kinase to inhibit cytokine induced protein and DNA synthesis. It is a late stage T cells and B cells activation inhibitor. RPM, as a novel immunosuppressant, not only can inhibit the immune cells, but also can hinder the proliferation and transmigration of vascular smooth muscle to reduce rejection reaction.

Mycophenolate mofetil, approved by American FDA, was applied in clinical rapidly. It has potent curative effects and a high selective effect on proliferative lymphocytes, as well as can prevent the formation of antibody through direct inhibition of B cells proliferation.

Due to the restrictions of selectivity and specificity, the above mentioned immunosuppressive agents will inevitably damage immune defense capacity of the patients when receiving the treatment, resulting in the descent anti-infection ability of patients, the increasing risk of malignant lesions, the injury of hematopoietic system, immune system, liver, kidney and gastrointestinal function, neural and endocrine function disorder, and inducing some allergic reactions, etc. For instance, cyclophosphamide may cause hair loss, and induce hemorrhagic cystitis, such as frequent micturition, urodynia, hematuria, and proteinuria; glucocorticoids may aggravate or induce infection, induce gastric ulcer, combined with hemorrhage and perforation, provoke metabolic disorders, raise blood pressure, blood glucose, and blood fat, cause osteoporosis, and evoke adverse reaction of insomnia by exciting central nervous system; azathioprine can cause cholestasis and hepatocellular damage; MTX induce canal damage symptoms, such as oral cavity ulcer, bloody stool, and so on, and can cause teratism and stillbirth; cyclosporin is toxic to kidney, liver and nervous system, and can lead to high blood pressure, secondary infection and onset of tumor; FK506 also has renal toxicity, even more than CsA in neurotoxicity, and causes damages on the islet β2 cells that induces diabetes; rapamycin can elicit leukopenia, thrombocytopenia and hyperlipidemia; mycophenolate mofetil can cause vomiting, diarrhea and other gastrointestinal symptoms, leukopenia, sepsis and high blood uric acid, hyperkalemia, myalgia or sleepiness, etc.

Sphingosine-1-phosphate enzyme receptor antagonist FTY720 and sphingosine (a kind of endogenous hemolytic lipid) have some structural similarities. Sphingosine is phosphorylated to form sphingosine-1-phosphatek enzyme, a homologous series ligands of its receptor family, induced by sphingosine enzyme. Activation of the receptor leads to the following physiological activities: cells differentiation, growth and survival, and regulations of cytoskeletal recombinant that can change adhesion and morphology of cells. In the normal immune responses, the proliferation of T lymphocytes and B lymphocytes is taken place in lymph nodes. They down-regulate the sphingosine-1-phosphate receptor expression when they are in the lymph nodes. Once their activation and proliferation are completed, they will up-regulate the number of sphingosine-1-phosphate receptor on cell surface, which allowed them to leave the lymph nodes. Lymphocyte sphingosine-1-phosphate enzyme receptors bind to their ligands resulting in the down-regulation of sphingosine-1-phosphate enzyme, and thus losing the function of separating from the lymph nodes. To the end, lymphocytes will adhere to the lymph nodes (1, 2, 3). Traditional immunosuppressive agents such as cyclosporin have the action mechanism of inhibiting activation of T lymphocytes and B lymphocytes. In contrast, sphingosine-1-phosphate enzyme receptor antagonist achieves the purpose by means of limiting lymphocytes within the lymph system other than impairing the immune responses by lymphocytes inactivation. Sphingosine-1-phosphate enzyme receptor antagonist can be used for the treatment of various transplant rejections and immune inflammatory diseases.

Sphingosine-1-phosphate enzyme receptor antagonist FTY720 was successfully developed by Novartis (Novartis), and conducted clinical trials on multiple sclerosis and transplant patients in America and Europe (4, 5), and has gotten through a phase II clinical trial. However, FTY720 acts on not only sphingosine-1-phosphate enzyme receptor-1 (S1P1), but sphingosine-1-phosphate enzyme receptor-3 (S1P3), therefore, it can cause side effects such as bradycardia (6).

SUMMARY

The present invention provides a heterocyclic group contained amino-methanol derivative, and salt, a synthetic method and use thereof.

The present invention relates to compounds of Formula I:

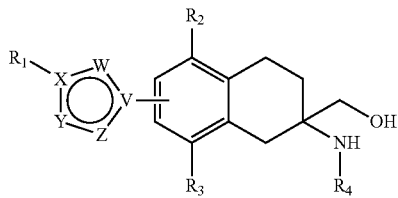

Formula I wherein $R_1$=alkyl, cycloalkyl, aryl, heterocyclyl;
$R_2$, $R_3$=hydrogen, halogen or alkyl;
$R_4$=alkyl, aryl methyl, carbonyl, alkyl sulfonyl;
W, Y, Z=C, CH, $CR_1$, N, O, S;
X, V=C, N.

Details of the invention are as follows:

As described above, except for special annotations, the following terms in the entire disclosure should be appreciated as follows:

Terms of "at least one", or "be substituted by one (followed by a known substituent)" are used to indicate the number of substituent groups connecting to a specific group, such as alkyl, cycloalkyl, heterocyclyl, aryl, heteroaryl, such as 1 to 6, or generally 1 to 4, for example, 1, 2 or 3, usually referring to one or two, or one substituent group.

"Alkyl" refers to an aliphatic hydrocarbon, straight chain or branched, comprising approximately 1 to 20 carbon atoms. The preferred alkyl contains about 1 to 8 carbon atoms, more preferably about 1 to 6 carbon atoms. In a particular embodiment, it is represented by C1-C3 if the alkyl contains 1 to 3 carbon atoms. Branched alkane is composed of one or more lower alkyl groups, such as methyl, ethyl or propyl, linked to a straight chain alkane. "Lower alkyl" refers to straight or branched chain having 1 to 6 carbon atoms. "Alkyl" can be either unsubstituted or substituted selectively with one or more the same or different substituents. The substituents is selected from the group consisting of halogen, alkyl, aryl, cycloalkyl, heterocyclyl, heteroaryl, cyano, hydroxy, alkoxy, sulfenyl, amino, aliphatic amine, cycloaliphatic amine, aliphatic diazo compounds, aliphatic ether (ester), aromatic ether (ester), aliphatic ring ether (ester), carboxylic acid, alkoxyl formyl. If no restrictions, a suitable alkyl may include methyl, ethyl, n-propyl, isopropyl, tert-butyl.

"Aryl" refers to an aromatic monocyclic or polycyclic system, consisting of about 6 to 14 carbon atoms, generally 6 to 10 carbon atoms. Aryl can be selectively substituted by one or more the same or different "ring substituents" (or "substituents at the ring"), like the definition of benzene. If no other restrictions, a suitable aromatic group includes phenyl, and naphthyl.

"Heteroaryl" refers to an aromatic monocyclic or polycyclic system, having about 5 to 14 ring atoms, preferably 5 to 10 ring atoms. Besides carbon atoms as ring atoms, one or more ring atoms are heteroatoms selected from the group consisting of nitrogen, oxygen and sulfur, which can exist separately or in combination. The preferred heteroaryl contains 5 to 6 ring atoms. Heteroaryl can be substituted by one or more the same or different ring substituents. The prefixes of nitrogen, oxygen, sulfur, before the root name of heteroaryl, implicate that at least one nitrogen, oxygen, or sulfur atom is as a ring atom, respectively. A nitrogen atom of heteroaryl can be oxidized into an N-oxide. "Heteroaryl" may also include the condensed ring of heteroaryl and aryl. The non-limiting examples of heteroaryl include pyridine, pyrazine, furan, thiophene, pyrimidine, pyridine (including N-substituted pyridine), isoxazole, isothiazole, oxazoline, thiazole, pyrazole, oxdiazole, pyrrole, pyrazole, triazole, 1,2,4-sulfdiazole, pyrazine, pyridazine, quinoxaline, phthalazine, oxindole, imidazole[1,2-A]pyridine, imidazole[2,1-B]thiazole, benzofuran, indole, azaindole, benzimidazole, benzothiophene, quinoline, imidazole, thienopyridine, quinazoline, pyrrole-pyridine, imidazole-pyridine, isoquinoline, benzene-azaindole, 1,2,4-triazine, benzothiazole and the like. The word "heteroaryl" also includes a saturated heterocyclyl (a heterocyclyl is also named as a heterocyclic group), e.g. tetrahydroisoquinoline, tetrahydroquinoline, etc.

"Cycloalkyl" refers to a non-aromatic monocyclic or polycyclic system containing 3 to 10 carbon atoms, preferably 5 to 10 carbon atoms, more preferably 5 to 7 carbon atoms. Cycloalkyl can be substituted by one or more the same or different ring substituents. The non-limiting examples of a suitable monocyclic cycloalkyl include: cyclopropyl, cyclopentyl, cyclohexyl, cycloheptane, etc. The non-limiting examples of a suitable polycyclic cycloalkyl include: decahydronaphthalene, norbornane, adamantane and the like.

"Halogen" refers to fluorine, chlorine, bromine, or iodine. The preferred are fluorine, chlorine and bromine.

"Heterocyclyl" or "heterocycle" refers to a non-aromatic saturated monocyclic or polycyclic system containing 3 to 10 ring atoms, preferably 5 to 10 ring atoms, which has one or more non-carbon atoms (e.g. 2, 3, or 4) in the ring system, such as nitrogen, oxygen, or sulfur. No two Oxygen and/or sulfur atoms are connected each other in the ring system. Heterocyclyl can contain 5 to 6 ring atoms. The prefixes of nitrogen, oxygen, sulfur, before the root name of heterocyclic, implicate that at least a nitrogen, oxygen, or sulfur atom is as a ring atom, respectively. Any amino forms in heterocyclic ring, such as some protected amino groups, for example, —N(BOC), N(CBZ)—N group (TOS) and the like can be considered as a part of the present invention. Heterocyclyl can be substituted by one or more the same or different ring substituents. The non-limiting examples of a suitable monocyclic heterocyclyl include piperidine, pyrrolidine, piperazine, morpholine, thiomorpholine, thiazolidine, dioxane, tetrahydrofuran, tetrahydrothiophene, lactam, lactone and the like.

"heteroaryl" can also mean a single group (e.g. carbonyl), which replaces two active hydrogen of the same carbon atom at the same time. For example, as shown in pyrrolidone:

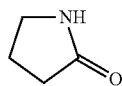

It is noted that the present invention in the heteroatom containing ring system, there is no hydroxyl connected to N, O or S atom at the carbon atom, similarly, for instance, in the ring:

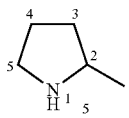

no —OH linked directly to the No. 2 and No. 5 carbon atoms.

It should also be noted that there are tautomeric forms, such as the following groups:

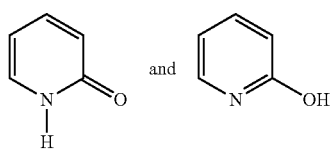

It is considered to be as a typical example in the present invention.

"Hydroxyalkyl" means an OH-alkyl group, wherein the alkyl was defined as above. The preferred includes lower alkyl, for example, hydroxyethyl.

The non-limiting examples of hydroxyalkyl groups include hydroxymethyl and 2-hydroxyethyl.

"Acyl" means H—C(O)—, —C(O)— linked to alkyl or cycloalkyl as defined above. The core structure is connected by carbonyl. The preferred are acyls containing lower alkyl groups. A suitable acyl group includes formyl, acetyl or propionic acid.

"Alkoxy" means an alkyl-O— group, herein the alkyl as previously described. A suitable non-limiting example of alkoxy includes methoxy, ethoxy, n-propoxy, isopropyl and n-butoxy. The core structure is connected by etheroxy.

The term "replaced" or "substituted" means in a specific atom, one or more hydrogens are replaced by specific groups. If the normal valence of the specific atom do not exceed in the existing circumstances, then the replacement results in a stable compound.

The substituents and/or variables are allowed to combine only if the combination results in stable compounds. The "stable compounds" or "stable structure" means a compound is capable of fully and effectively being isolated to be a available purity degree in the reaction mixture, and becomes an effective ingredient of medication.

The term "replaced selectively" or "substituted selectively" means selective replacement can be taken by using specified groups, free radicals or other groups.

The term "purification", "pure form" or "in the form of isolation and purification" refers to the physical state of a compound isolated after a synthesis process (e.g. from a reaction mixture), crude drug, or a combination. Therefore, for a compound, the term "purification", "in a purified form" or "in the form of separation and purification" refers to the physical state of a compound is in the state after purification process or after the processing described herein with known skills (such as chromatographic separation, recrystallization, etc.). According to the standard requirements, in a sufficient purity, the analysis technology described herein or a famous high-level skill is also characteristic.

It is also worth noting that in the specification, routes, examples and tables of the present invention, any carbon atoms and heteroatoms that do not satisfy the valence principle are assumed to contain a sufficient number of hydrogen atoms to satisfy the valence principle.

When a functional group of a compound is called "protected", it means that the functional group is in the modified form to prevent the unwanted side reactions occurring in the reaction. Suitable protective groups will be verified by the general operation technology of organic experiment and methods mentioned in the standard textbooks (e.g. T. W. Greene et al, Protective Groups in organic Synthesis (1991), Wiley, N.Y.).

When any variable groups (e.g. aryl, heterocyclyl, R2, etc.) appear more than once in any component or chemical formula (I), each change in the definition of the group is independent from others.

As used herein the word "composition", the purpose of it is to obtain a result directly or indirectly from combination of particular components in a specific quantity and any products combined from particular components in a specific quantity.

Herein prodrugs and solvates of the compounds in this invention are also carefully considered. Discussions concerning about prodrugs are provided in Pro-drugs as Novel Delivery Systems (1987) Vol. 14 of the A.C.S. Symposium Series, Bioreversible Carriers in Drug Design, (1987) Edward B. Roche, ed., American Pharmaceutical Association, written by T. Higuchi and V. Stella, and in the Pergamon Press. The word "prodrug(s)" means a compound (e.g. a drug precursor) is transformed in vivo into a compound of Formula (1), or pharmaceutical salt, hydrate or solvate thereof. This transformation may be taken place by multiple mechanisms (e.g.

metabolism or chemical process), such as hydrolysis in the blood. Discussions about the application of prodrugs are provided in "Prodrugs as Novel Delivery Systems," Vol. 14 of the A.C.S. Symposium Series, Bioreversible Carriers in Drug Design, ed. Edward B. Roche, American Pharmaceutical Association, written by T. Higuchi and W. Stella, and in Pergamon Press, 1987.

For example, there is a hydroxyl group in a compound of Formula (I), then a prodrug thereof can be obtained from replacing the hydrogen atom in hydroxyl group by another substituent group. For instance, the substituent group can be (C1-C6)alkyl acyloxy methyl, 1-((C1-C6)alkyl acyloxy) ethyl, 1-methyl-1-((C1-C6)alkyl acyloxy)ethyl, (C1-C6) alkoxycarbonyl-O-methyl, N—(C1-C6) alkoxycarbonyl amino methyl, -succinyl, (C1-C6)alkanoyl, -amino (C1-C4) alkyl, -aryl acetyl and -aminoacyl, or -aminoacyl-aminoacyl, wherein each aminoacyl is independently choosing from natural L-amino acids, P(O)(OH)2, —P(O)(O(C1-C6) alkyl)2 or glycosyl (the most fundamental reason is the removal of a hydroxy existing in the form of hemiacetal in carbohydrate), etc.

According to an amino group existing in a compound of Formula (1), the prodrug of the compound can be obtained from replacing the hydrogen atoms in the amino group by other substituent groups. For instance, these substituent groups can be R-carbonyl, RO-carbonyl, NRR'-carbonyl (R and R' are independent), (C1-C10)alkyl, (C3-C7)cycloalkyl, phenyl, or R-carbonyl (-amino acyl is the natural existence or natural-amino acyl), —C(OH)C(O)OY1, wherein Y1 is H, (C1-C6)alkyl or phenyl, —C(OY2)Y3 wherein Y2 represents (C1-C4)alkyl and Y3 represents (C1-C6)alkyl, carbonyl (C1-C6) alkyl, amino (C1-C4)alkyl, or one-N— or di-N, N—(C1-C6)alkylamino alkyl, —C(Y4)Y5 wherein Y4 represents hydrogen or methyl and Y5 represents one-N— or di-N,N—(C1-C6)morpholino alkylamino, piperidine-1-yl or pyrrolidine-1-yl, etc.

One or more compounds in the present invention may exist in the forms of non-solvates, and solvates just similar as the solvates formed from the pharmaceutically acceptable solvents such as water and ethanol. Therefore, the invention herein includes solvates and non-solvates of the compounds of Formula (I). "Solvate(s)" refer to the physical aggregates of a compound of the present invention and one or more solvent molecules, which include ions in different degrees and covalent bonds, such as hydrogen bonds. It has been confirmed that the solvates can be separated, for example, when the crystal lattice of the crystal was mixed in one or more solvent molecules. "Solvate(s)" contain two parts, the solvent phase and the separable solvate. There are quantities of solvate examples, including ethanol solvate, methanol solvate, etc. "Hydrate(s)" is a kind of solvates whose solvent molecules are water ($H_2O$) molecules.

One or more compounds of the present invention can be arbitrarily prepared into solvates. The preparation methods of the solvates are well known. For example, it is described in M. Caira et al, J. Pharmaceutical Sci., 93 (3), 601-611 (2004), the method for preparing antifungal fluconazole solvates prepared by ethyl acetate and water. It is also described a similar preparation method of solvates and hydrates in E. C. van Tonder et al, AAPS PharmSciTech., 5 (1), article 12 (2004); and A. L. Bingham et al, Chem. Commun., 603-604 (2001). A typical, non-limiting preparation process is that at a temperature higher than normal temperature, dissolve the compound of the present invention into the required amount of the ideal solvent (organic solvent or water or mixed solvent of the above two), lower the temperature, lay and crystallize, and then separate out the crystal by using the standard methods. By I. R. spectroscopy analysis technology, it can be confirmed that the existence of the solvent (water) in the solvates (hydrate).

"Effective amount" or "therapeutically effective amount" refers to the amount of the compound of the present invention or a composition exhibits a significant effect in inhibiting the said diseases, and thus produces necessary therapeutic, improving, inhibiting or preventing effects.

The salt of a compound of Formula I also belongs to the present invention. Except specific indications, its salt can be understood according to a compound of Formula I. The salt in the invention refers to the acid salt formed by organic acid/inorganic acid, and the basic salt formed by organic alkali/inorganic alkali. In addition, when the basic functional group of a compound of Formula I is a pyridine or imidazole (but not limited to pyridine or imidazole), and acidic functional group is a carboxylic acid (but not limited to carboxylic acid), a zwitterion (inner salt) will be formed, which is also included in the salt of the invention.

Although other salts are also useful, it is preferred to choose pharmaceutically acceptable salts (e.g., non-toxic, physiologically acceptable). The salt of a compound represented by Formula I is formed by the compound and the same amount of acid/base by reaction in medium for the precipitation of the salt, or by cryodesiccation in aqueous medium.

Exemplary acid salts include: acetic acid salts, ascorbate salts, benzoate, benzene sulfonates, hydrogen sulfates, borates, butyrates, citrates, camphorated, camphorsulfonates, fumarates, hydrochlorides, hydrobromides, hydroiodides, lactates, maleates, mesylates, napsylates, nitrates, oxalates, phosphates, propionates, salicylates, succinates, sulfates, tartrates, thiocyanates, tosylates, etc. Some other acids are commonly acknowledged to be suitable for producing the pharmaceutically valuable salts for low-level drug compounds, and have been discussed, for example, in P. Stahl, Camilie G et al. Handbook of Pharmaceutical Salts: properties, selection and use. (2002) Zurich: Wiley-VCH; S. Berge, et al. Journal of Pharmaceutical Sciences, (1977) 66(1) 1-19; P. Gould, World Journal of Pharmaceutical Sciences (1986) 33 201-217; Anderson, et al., The Practice of Medicinal Chemistry (1966), Academic Press, New York; Orange Book (Food and Drug Administration, Washington, D.C. Columbia website). In addition, the publications are all incorporated herein by references.

Typical basic salts include ammonium salts, alkali metal salts, such as sodium salts, lithium salts and potassium salts; alkaline-earth metal salts, such as calcium salts and magnesium salts; salts formed by organic bases (such as organic amines), for example, dicyclohexyl amine, tertiary butyl amines; as well as salts formed by amino acids, such as arginine, or lysine and the like. The lower nitrogen containing species can be divided into four parts by medium: lower alkyl halide (e.g. methyl, ethyl, or butyl chloride, bromide and iodide); dialkyl sulfates (e.g. dimethyl, diethyl and dibutyl sulfates); long chain halides (e.g. decyl, lauryl and octadecyl chlorides, bromides and iodides); aralkyl halides (e.g. benzyl and phenethyl bromides).

All the acid salts and basic salts are intended to be pharmaceutically acceptable salts within the scope, and all of the acid and basic salts for the purpose of invention are identified as free form equivalent to the corresponding compounds.

In the present invention, pharmaceutically acceptable esters include following groups: (1) carboxylic esters after esterification of hydroxyl groups, wherein carbonyl-free moieties of the esters are selected from the following: straight or branched alkyl, (e.g. acetyl, propyl, tertbutyl or n-butyl), alkoxyalkyl (e.g. methoxymethyl), aralkyl (e.g. benzyl), aryloxy alkyl (e.g. phenoxy methyl), aryl (e.g. phenyl selectively substituted by halogen, C1-4 alkyl or C1-4 alkoxy or amino); (2) sulfonic acid esters, such as alkyl or aralkyl sulfonyl (e.g. mesyl) (3) amino acid esters (e.g. L-valine acyl or L-isoleucine acyl); (4) phosphoric acid esters, for example, monophosphate, diphosphate or triphosphate; (5) phosphoric acid esters can be further esterified, such as by C1-20 alcohols or the reactive derivatives thereof, or by 2,3-di(C6-24)acyl glycerol.

The compounds of Formula I and the salts, solvates, esters and prodrugs thereof have their tautomeric forms (e.g. amides or imides). All these tautomeric forms are expected to be parts of the present invention.

The compounds of Formula I contain asymmetric or chiral centers, hence have various stereoisomers. All stereoisomers as well as the mixtures thereof, including the racemic mixture, are parts of the present invention. In addition, the present invention includes all geometrical and positional isomers. For example, if a compound of Formula I contains a double bond or a fused ring, either cis or trans isomer, or mixtures thereof, are within the scope of the invention.

A diastereomeric mixture can be separated into various individual diastereomers, on the basis of the different physical chemical properties by means of known measures. For example, enantiomers can be separated through reaction with suitable optical active substances (such as chiral alcohols or Mosher's Morse acyl chloride) into diastereomers which are separated then and transformed (such as hydrolysis) into the various corresponding individual isomers. Some compounds of the Formula I which are probably atropisomers (such as substituted aryl) are also parts of the invention. Enantiomers can also be separated by using chiral chromatographic column.

The compounds of Formula I may exist in different tautomeric forms, which are all included within the scope of the present invention. For example, compounds in keto-enol and imine-enamine forms.

The invention also includes isotope labeled compounds. In fact, it is common that one or more atoms are replaced by an atom different in atomic mass or mass number in nature. Isotopes included in the compound of the present invention include H, C, N, O, P, F, S, such as $^2H$, $^3H$, $^{13}C$, $^{14}C$, $^{15}N$, $^{18}O$, $^{17}O$, $^{31}P$, $^{32}P$, $^{35}F$ and $^{36}S$.

It is very useful for the isotope labeled (such as $^3H$ and $^{14}C$) compounds of Formula I in the substances and/or tissues distribution detections. Isotope tritium ($^3H$) and $^{14}C$ ($^{14}C$) are widely applied since easily prepared and detected. In addition, compounds substituted by deuterium ($^2H$) displayed advantageous therapeutic effects and better metabolic stability (such as increasing half life period in vivo, or reducing desire dose), hence they are useful in some cases. The synthesis process of the isotope labeled compounds of Formula I refers to the published documents and/or the examples herein.

The present invention also includes the polymer, salt, solvate, ester, and prodrug of a compound represented by Formula I.

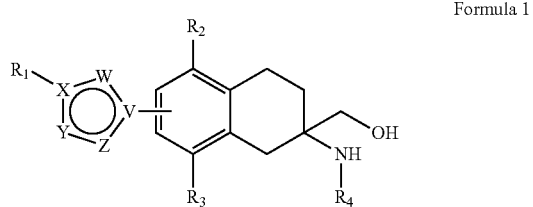

Formula 1

In some embodiments, $R_1$ in Formula I is:

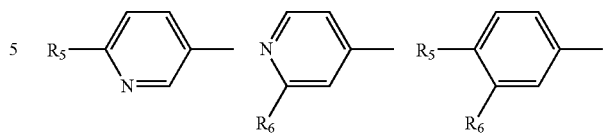

In some other embodiments, in Formula I, $R_1=$

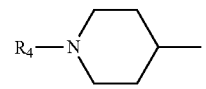

$R_4$=alkyl allyl, benzyl, —C(=O)CH$_3$, —C(=O)R, —SO$_2$CH$_3$, —SO$_2$R(R=alkyl), aryl methyl, carbonyl, alkyl sulfonyl;
$R_5$=alkyl, alkoxy or $R_7$OCH$_2$CH$_2$O—,
$R_6$=H, alkyl or fluoroalkyl,
$R_7$=alkyl
In some embodiments, in Formula I,

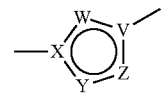

can be

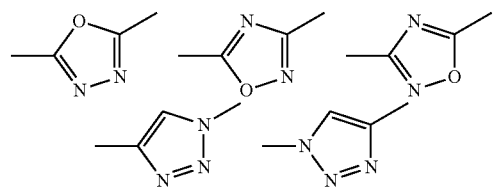

In some other embodiments, $R_2$ and $R_3$ in Formula I are independently H, halogen, and alkyl.

In some embodiments, the compound of Formula I can be selected from the followings:

Example 1, 6-[5-(4-methoxyphenyl)-2-[1,3,4]oxdiazolyl]-2-amino-1,2,3,4-tetrahydro-naphthalen-2-yl-methanol Example 2, 6-[5-(4-ethoxyphenyl)-2-[1,3,4]oxdiazolyl]-2-amino-1,2,3,4-tetrahydro-naphthalen-2-yl-methanol Example 3, 6-[5-(4-fluorophenyl)-2-[1,3,4]oxdiazolyl]-2-amino-1,2,3,4-tetrahydro-naphthalen-2-yl-methanol Example 4, 6-[5-(3-fluorophenyl)-2-[1,3,4]oxdiazolyl]-2-amino-1,2,3,4-tetrahydro-naphthalen-2-yl-methanol Example 5, 6-[5-(2-fluorophenyl)-2-[1,3,4]oxdiazolyl]-2-amino-1,2,3,4-tetrahydro-naphthalen-2-yl-methanol Example 6, 6-[5-(4-pyridyl)-2-[1,3,4]oxdiazolyl]-2-amino-1,2,3,4-tetrahydro-naphthalen-2-yl-methanol Example 7, 6-[5-(4-piperidyl)-2-[1,3,4]oxdiazolyl]-2-amino-1,2,3,4-tetrahydro-naphthalen-2-yl-methanol Example 8, 1-{4-[5-(6-hydroxymethyl-6-amino-5,6,7,8-tetrahydro-naphthalen-2-yl)-2-[1,3,4]oxdiazolyl]-1-piperidyl}ethanone Example 9, 6-[5-(3-methyl-4-methoxy phenyl)-2-[1,3,4] oxdiazolyl]-2-amino-1,2,3,4-tetrahydro-naphthalen-2-yl-methanol Example 10, 7-{5-[4-(2-methoxyethoxy)phenyl]-2-[1,3,4]oxdiazolyl]-2-amino-1,2,3,4-tetrahydro-naphthalen-2-yl-methanol Example 11, 7-[5-(3-trifluoromethyl-4-iso propoxyphenyl)-2-[1,3,4]oxdiazolyl]-2-amino-1,2,3,4-tetrahydro-naphthalen-2-yl-methanol Example 12, 6-[5-(3-nitro-4-pyridyl)-3-1,2,4-oxdiazolyl]-2-amino-1,2,3,4-tetrahydro-naphthalen-2-yl-methanol Example 13, 7-[5-(2-hydroxymethyl-4-pyridyl)-2-1,3,4-oxdiazolyl]-2-amino-1,2,3,4-tetrahydro-naphthalen-2-yl-methanol Example 14, 4-[5-(7-hydroxymethyl-7-amino-5,6,7,8-tetrahydro-naphthalen-2-yl)-1,3,4-oxdiazolyl]-1-indenol Example 15, 7-[5-(4-methoxy-3-methyl phenyl)-2-1,3,4-oxdiazolyl]-2-amino-1,2,3,4-tetrahydro-naphthalen-2-yl-methanol Example 16, 7-[5-(4-isopropoxyphenyl)-2-1,3,4-oxdiazolyl]-2-amino-1,2,3,4-tetrahydro-naphthalen-2-yl-methanol Example 17, 7-{5-[4-(2-methoxyethoxy)-3-trifluoromethyl phenyl]-2-1,3,4-oxdiazolyl}-2-amino-1,2,3,4-tetrahydro-naphthalen-2-yl- methanol Example 18, 7-{5-[4-(2-methoxyethoxy)-3-methyl phenyl]-2-1,3,4-oxdiazolyl}-2-amino-1,2,3,4-tetrahydro-naphthalen-2-yl-methanol Example 19, 7-[5-(6-isopropoxy-3-pyridyl)-2-1,3,4-oxdiazolyl]-2-amino-1,2,3,4-tetrahydro-naphthalen-2-yl-methanol Example 20, 7-[5-(3,4-diethoxyphenyl)-2-[1,3,4]-oxdiazolyl]-2-amino-1,2,3,4-tetrahydro-naphthalen-2-yl-methanol Example 21, 2-(7-benzylamino-5,6,7,8-tetrahydro-7-naphthalenemethanol)-5-(3-methyl-4-isopropoxy)-1,3,4-oxdiazole Example 22, 2-(7-amino-5,6,7,8-tetrahydro-7-naphthalenemethanol)-5-(3-methyl-4-isopropoxy)-1,3,4-oxdiazole Example 23, 7-[5-(3-methyl-4-isopropoxyphenyl)-2-1,3,4-oxdiazolyl]-2-ethylamino-1,2,3,4-tetrahydro-naphthalen-2-yl-methanol Example 24, 7-[5-(3-methyl-4-isopropoxyphenyl)-2-1,3,4-oxdiazolyl]-2-dimethylamino-1,2,3,4-tetrahydro-naphthalen-2-yl-methanol Example 25, N-{2-hydroxymethyl-7-[5-(3-methyl-4-isopropoxyphenyl)-2-1,3,4-oxdiazolyl]-1,2,3,4-tetrahydro-naphthalen-2-yl}acetamide Example 26, N-{2-hydroxymethyl-7-[5-(3-methyl-4-isopropoxyphenyl)-2-1,3,4-oxdiazolyl]-1,2,3,4-tetrahydro-naphthalen-2-yl}methanesulfonamide Example 27, 7-[3-(3-methyl-4-isopropoxyphenyl)-5-1,2,4-oxdiazolyl]-2-amino-1,2,3,4-tetrahydro-naphthalen-2-yl-methanol Example 28, 6-[3-(3-methyl-4-isopropoxyphenyl)-5-1,2,4-oxdiazolyl]-2-amino-1,2,3,4-tetrahydro-naphthalen-2-yl-methanol Example 29, 7-[5-(3-methyl-4-isopropoxyphenyl)-3-1,2,4-oxdiazolyl]-2-amino-1,2,3,4-tetrahydro-naphthalen-2-yl-methanol Example 30, 6-[5-(3-methyl-4-isopropoxyphenyl)-3-1,2,4-oxdiazolyl]-2-amino-1,2,3,4-tetrahydro-naphthalen-2-yl-methanol Example 31, 7-[4-(3-methyl-4-isopropoxyphenyl)-1-1,2,3-triazolyl]-2-amino-1,2,3,4-tetrahydro-naphthalen-2-yl-methanol Example 32, 6-[4-(3-methyl-4-isopropoxyphenyl)-1-1,2,3-triazolyl]-2-amino-1,2,3,4-tetrahydro-naphthalen-2-yl-methanol, and physiologically acceptable salts thereof.

As described in the present invention, the salts of the compounds, i.e., the derivatives of 2-amino-1,2,3,4-tetrahydronaphthyl-2-methanol containing various substituents, are the salts of hydrochloric acid.

The methods for preparing the derivatives of 2-amino-1,2,3,4-tetrahydronaphthyl-2-methanol containing various substituents as described in the present invention include the reactions and synthetic steps as shown below:

Reaction Scheme 1

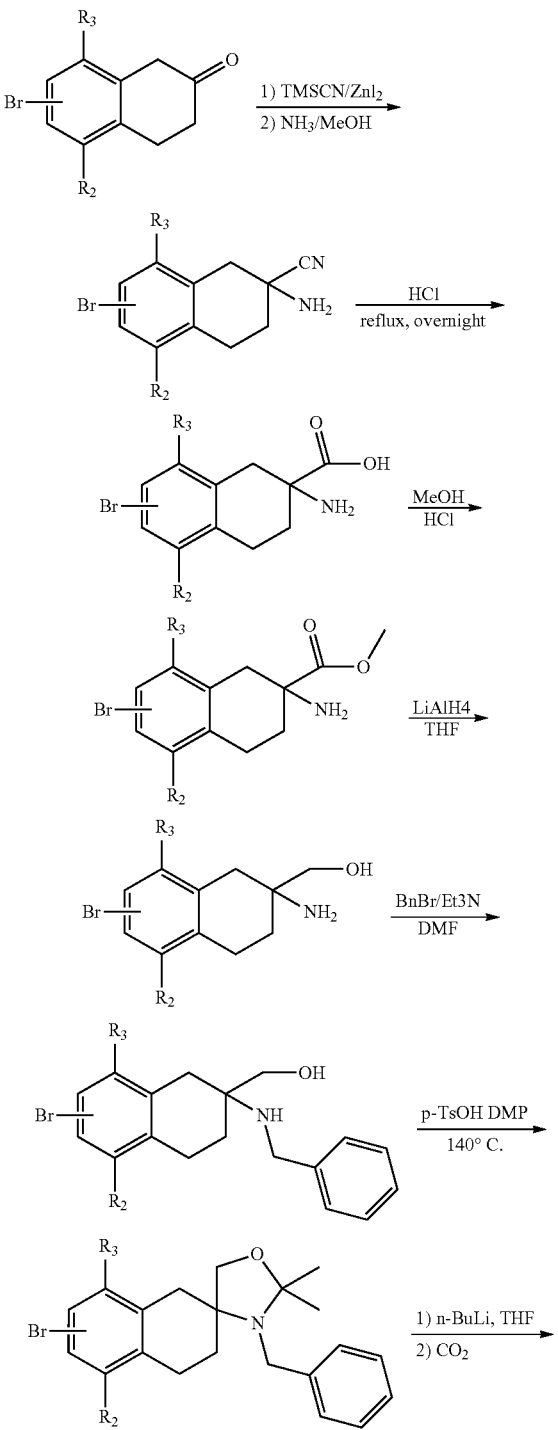

13
-continued
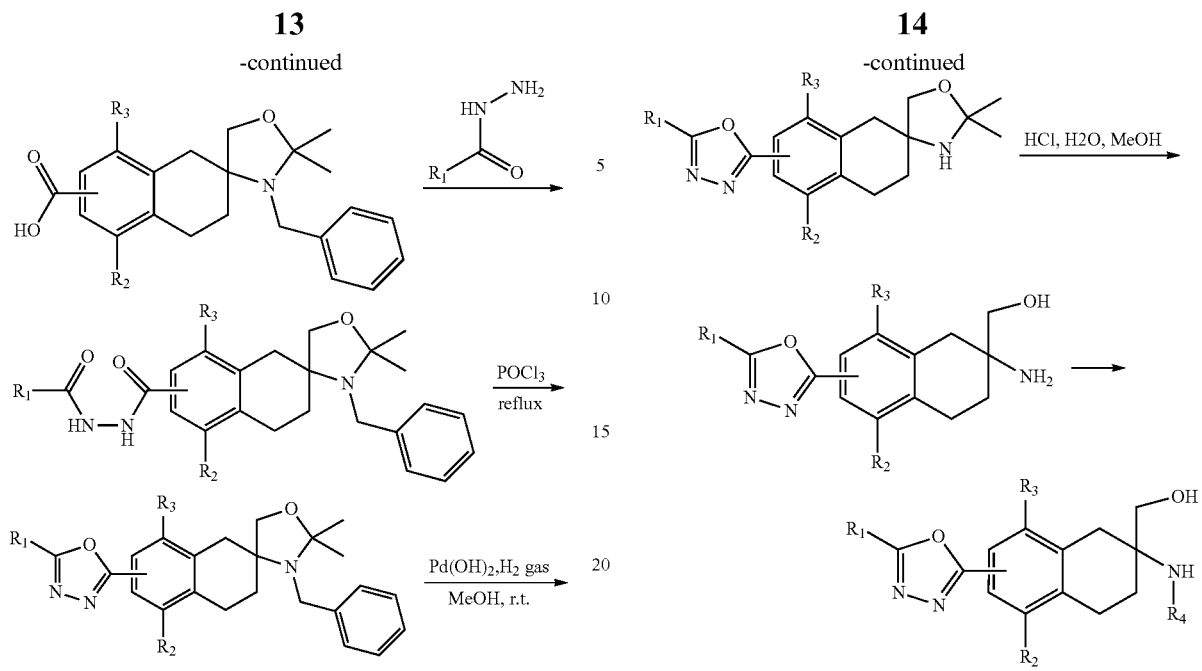
Reaction Scheme 2
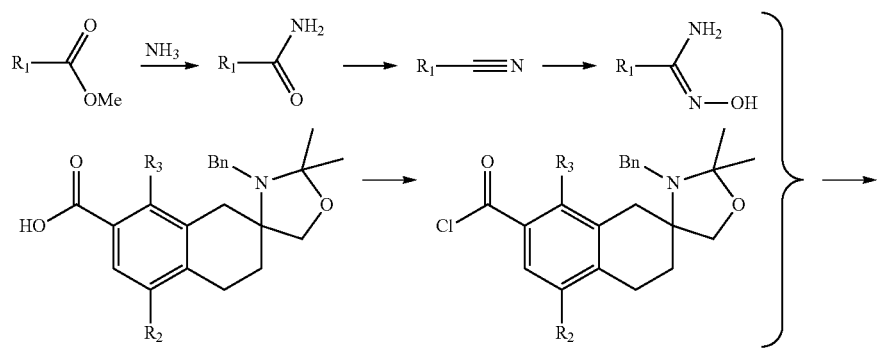
14
-continued
Reaction Scheme 3
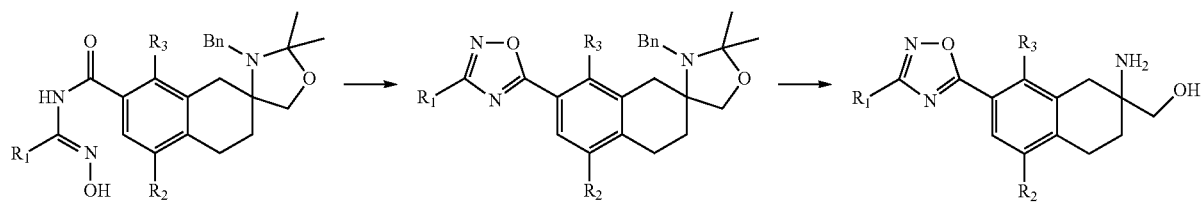
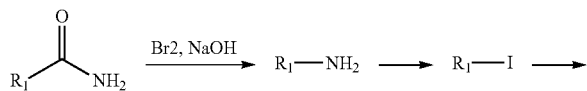

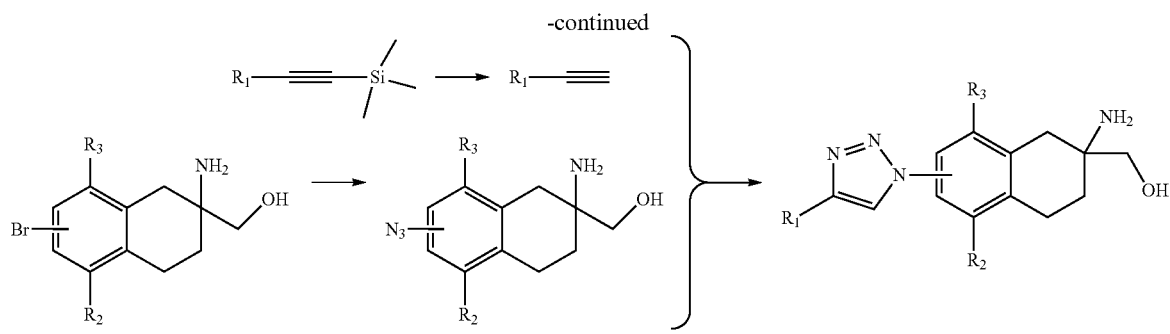

The present invention provides a heterocyclic group contained amino-methanol derivative, and the salt thereof in the preparation of immunosuppressive drugs.

The present invention provides a heterocyclic group contained amino-methanol derivative, and the salt thereof in the preparation of drugs for treating transplant rejection.

The present invention provides a heterocyclic group contained amino-methanol derivative, and the salt thereof in the preparation of drugs for the treatment of immune mediated inflammatory diseases (or immune inflammatory diseases).

The present invention provides a heterocyclic group contained amino-methanol derivative, and the salt thereof in the preparation of drugs for the treatment of multiple sclerosis, systemic lupus erythematosus and rheumatoid arthritis.

The compounds according to the invention can also exist in various polymorphic forms, such as amorphous and crystalline polymorphic forms. It is a further aspect of the present invention that all the polymorphic forms of the compounds according to the invention are included in the scope of the present invention.

As described below, all the phrases "compounds of the Formula (I)" refer to the compounds of Formula (I), and the salts, solvates or physiologically functional derivatives thereof as described herein.

The amount of the compound of formula (I) for reaching the desire biological effect depends on numerous factors, such as the specific compound, the specific use, administration regime and the condition of the patient. Generally, the daily dosage is from 20 mg to the 200 mg, e.g., from 20 mg to 50 mg. For the prevention or treatment of the above diseases, the compound of Formula (I) may be used alone, but a pharmaceutical composition containing the compound and some tolerable excipients are preferably. Excipients must be tolerable in the respects of being compatible with other components of the composition and harmless to the patient's health. The excipients may be solid or liquid, or both, preferably prepared in combination of the compound according to the invention into a single unit dose, such as a tablet, which may contain 0.05 to 95 weight percent of the compound. The composition may include other pharmaceutically active substances including other compounds according to Formula (I). The pharmaceutical composition according to the invention can be prepared through one of the known pharmaceutical preparation methods, which are essentially mixing the components and pharmaceutically acceptable excipients and/or auxiliaries.

The pharmaceutical composition of the invention are those which is suitable for oral, rectal, local, peroral, (e.g. sublingual) and parenteral (such as subcutaneous, intramuscular, intradermal or intravenous) administration. However, the most suitable administration route for each specific case depends on the property and severity of the disease in each case and the properties of the compound of Formula (I). Sugar coated preparation and sugar coated delayed-release preparation are also included in the scope of the present invention. Acid resistant and enteric preparations are preferred. Suitable enteric coatings include cellulose acetate phthalate, polyethylene acetate phthalate, hydroxypropyl methyl cellulose phthalate and anionic polymer of methacrylic acid and methacrylate.

The pharmaceutical compositions suitable for oral administration may be an individual unit dosage, such as a capsule, a cachet, a plating or tablet, each of them containing certain amount of a compound of Formula (I); powder or granule; solution or suspension in aqueous or anhydrous liquid; emulsion of oil in water or water in oil. As mentioned above, the composition may prepared through any suitable pharmaceutical methods, comprising the step of contacting the active compound with excipients (can be composed of one or more other components). In general, the composition is prepared by uniformly mixing the active compound and the liquid and/or fine crushing solid excipients, and molding the product if necessary. Thus, for example, the tablet may be prepared by compression of the compound: if appropriate, in combination with one or more additional components powder or granules or make them molding. Compressed tablets can be prepared, in the appropriate machinery, by firstly mixing the free flow form (such as powder or granular form) of the compound, if appropriately, with adhesives, lubricants, inert diluents and/or a kind of (amounts of) surfactants/dispersants, and then pressing into tablets. Molded tablets can be prepared, in the appropriate machinery, by moulding the powder compounds wetting by inert liquid diluents.

The pharmaceutical compositions suitable for oral administration (sublingual) include lozenge, which contains compounds of Formula (I) and corrigent (e.g., sucrose and Arabic gum), and pastille, which contains the compound in an inert medium such as gelatin and glycerol or sucrose and Arabic gum.

The pharmaceutical compositions suitable for parenteral administration preferably include sterile aqueous preparation of the compounds of Formula (I), which are preferably isotonic with the blood of subjects. The pharmaceutical compositions are preferably administered intravenously, and may also administered subcutaneously, intramuscularly or intradermally. These compositions can be preferably prepared, by mixing the compounds and water to obtain a solution, and then make the solution sterile and isotonic with blood. The injectable compositions according to the present invention generally comprise 0.1 to 5% of active compounds in weight.

The pharmaceutical compositions suitable for rectal administration are preferably single dose suppositories. They may be prepared, by mixing compounds of Formula (I) with one or more conventional solid excipients, such as cocoa butter, and molding the obtained mixture.

The pharmaceutical compositions suitable for topical administration are preferably ointment, cream, paste, spray, aerosol or oil. The available excipients are petroleum Jelly, lanolin, polyethylene glycol, alcohol and combinations of two or more of these above substances. The concentration of active compounds generally accounts for 0.1 to 15% of the weight of the composition.

Cutaneous penetration is feasible. The pharmaceutical compositions suitable for cutaneous penetration can be single patches, which are suitable for long close contact with the patient skin. This kind of patch relates to optional buffered aqueous solutions containing active compounds, and the compounds are dissolved and/or dispersed in adhesives or dispersed in polymers. The suitable concentration of active compounds is arranged from 1% to 35%, preferably from about 3% to 15%. It is especially possible that active compounds may be released through electron transportation or iontophoresis, e.g., as described in Pharmaceutical Research, 2 (6): 318 (1986).

The compounds of the present invention and the physiological salts thereof only target sphingosine 1 phosphate receptor 1. (S1P1), down-regulate S1P1 expression, and inhibit lymphocytes into the peripheral blood circulation, which are useful for the treatment of immune mediated inflammatory diseases such as multiple sclerosis, rheumatoid arthritis, etc.

In the graph, compound 179 is in Example 21, and compound 067 is in Example 22.

Figure 1:
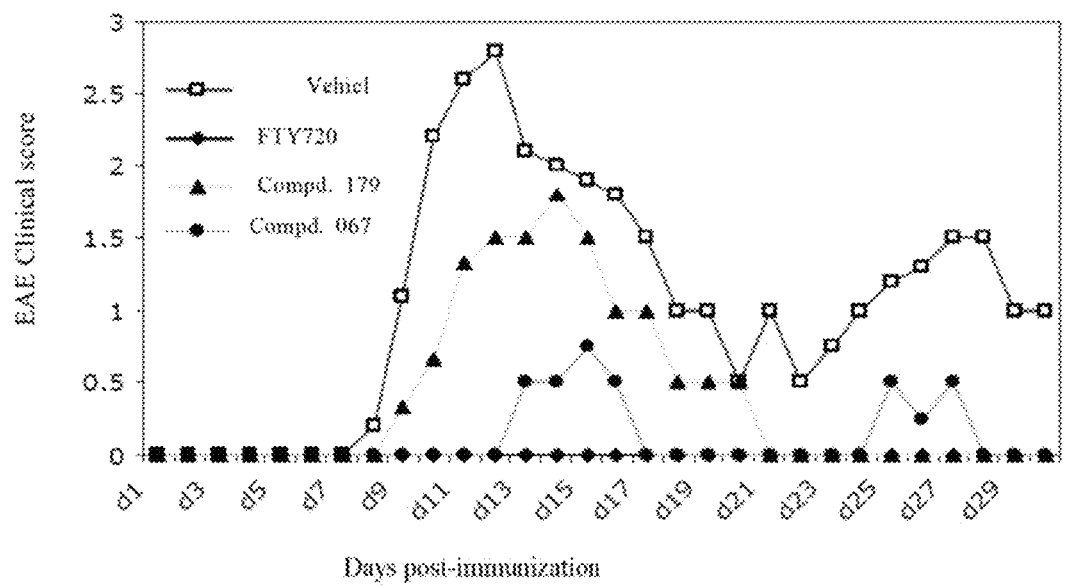
FIG. 1 is a graph that shows compounds obtained in Example 21 and Example 22 obviously inhibiting inducement and initiation of autoimmune multiple sclerosis.
Figure 2:
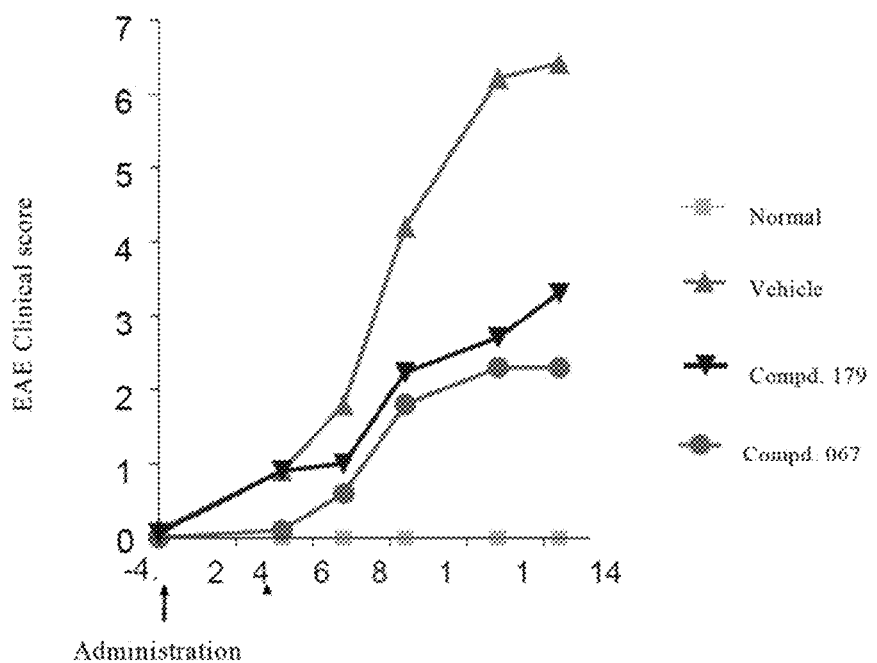

FIG. 2 is a graph that shows compounds obtained in Example 21 and Example 22 obviously inhibiting inducement and initiation of experimental rheumatoid arthritis;

In the graph, compound 179 is in Example 21, and compound 067 is in Example 22.

EMBODIMENTS

Experimental Parts

1. Synthesis of Compounds:
1. The LCMS analysis conditions in the synthesis process are as shown below:
LC Analysis

| | |
|---|---|
| Instrument model | Shimadzu LCMS-2020 System. |
| HPLC column: | XBridge C18 3.5 um 3.0 × 50 mm. |
| Column temperature | 40° C. |
| PDA wavelength: | 254 nm. |
| LC Pump Total Flow: | 1 ml/min. |
| Pump A: | 0.05% Formic acid solution in water; |
| Pump B: | 0.05% Formic acid solution in acetonitrile |
| LC Time Program: | 0-2.1 min, Pump B 5-100%; |
| | 2.1-3.5 min, Pump B 100%; |
| | 3.51 min, Pump B 5%; |
| | 6.5 min, Stop. |
| MS API Unit: | ESI; |
| MS Scan m/z: | 100-800(Event 1, Event2). |
| Result | [M − H ]$^-$, [M + H]$^+$ |

2. Synthesis

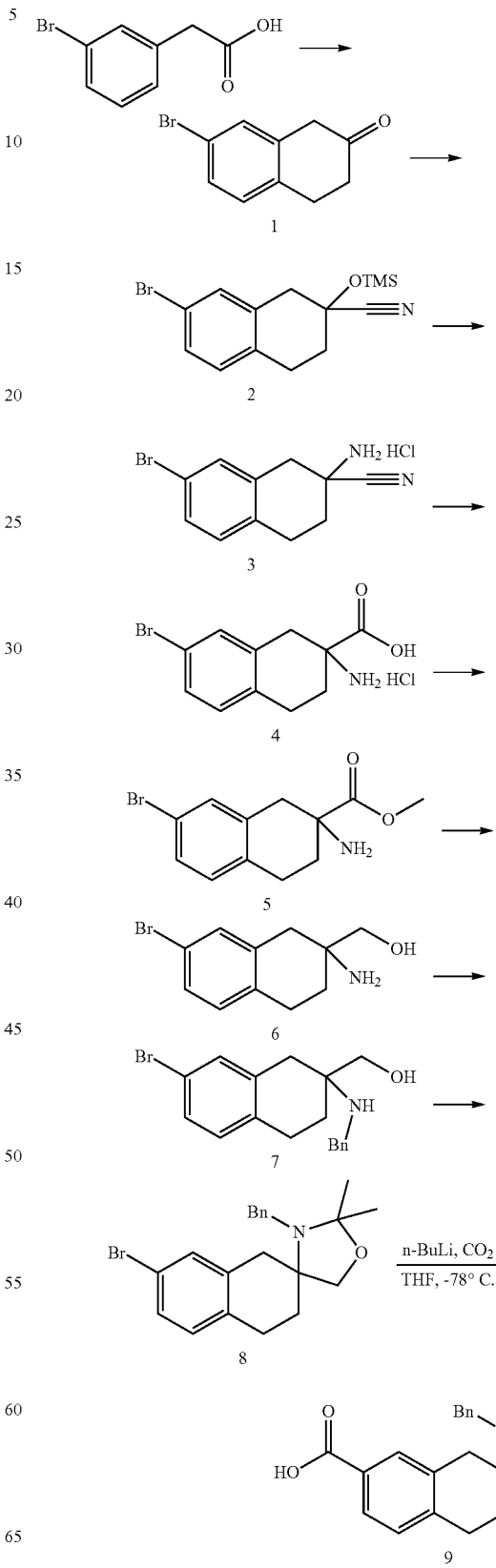

Reaction Scheme 4: Preparation of Intermediate 9

Preparation of Intermediate 1:

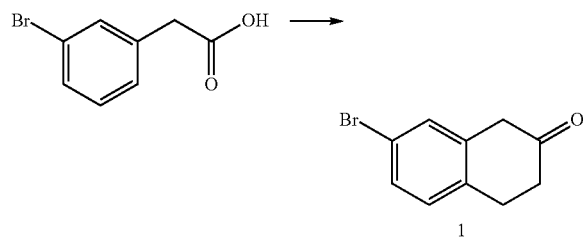

The raw material meta-bromophenylacetic acid (100 g, 0.47 mol, 1.0 eq) was dissolved in dichloromethane (500 ml), then was cooled to 0° C. in ice-salt bath. Oxalyl chloride (120 g, 0.95 mol, 2.0 eq) was added dropwise to the reaction mixture with temperature maintaining 0° C. After the dropping was finished, the reaction temperature was changed to room temperature and reacted for two hours. The reaction mixture was concentrated under reduced pressure to obtain meta-bromophenylacetyl chloride (110 g, 0.47 mol) after the reaction completed. The obtained meta-bromophenylacetyl chloride was dissolved in dichloromethane (200 ml) for further use.

$AlCl_3$ (210 g, 1.9 mol, 4.0 eq) and dichloromethane (500 ml) were added to another reaction flask. The system was cooled to −5° C. in ice-salt bath, and was dropped into the solution of the prepared meta-bromophenylacetyl chloride in dichloromethane described above, maintaining the temperature of −5° C., then ethylene gas was introduced into the system maintaining the temperature between −5° C.~0° C., with continuously three hours of ethylene gas. After completion of the reaction, the reaction mixture was poured into ice water (5000 ml), which was then extracted with dichloromethane (3×1000 ml). The organic layer were combined and washed once with water (1000 ml), dried over anhydrous $Na_2SO_4$, and filtered. The mother liquor was concentrated under reduced pressure to obtain a residue, which was then purified by column chromatography (ethyl acetate:heptane=1:30) resulting in intermediate 1 (45 g, yield: 43%) as a yellow solid. MS (M+H$^+$): 225, 227, the theoretical calculating value: 225, 227.

Preparation of Intermediate 3:

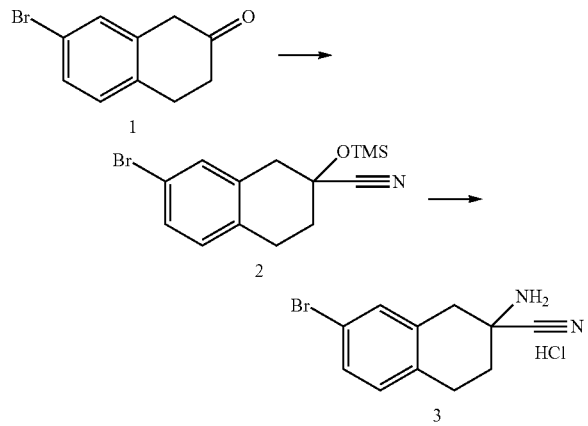

Under the protection of nitrogen, raw material of 1 (20.0 g, 89 mmol, 1.0 eq) and ZnI (1.4 g, cat.) were added to trimethyl silylcyanide (13.0 g, 130 mmol, 1.5 eq), and the reaction system reacted at room temperature for 3 hours to produce 2 $NH_3$/methanol solution (50 ml) was added to the reaction system, and then reacted at room temperature over night. After the reaction completed, the system was concentrated under the reduced pressure, and the resulting residue was dissolved in HCl/methanol (50 ml). Diethyl ether (200 ml) was added and large amounts of solid precipitated, then filtered, and the filter cake was dried to obtain intermediate compound 3 (23 g, 89%) as a yellow solid. MS (M+H$^+$): 251, the theoretical calculating value: 251.

Preparation of Intermediate 4:

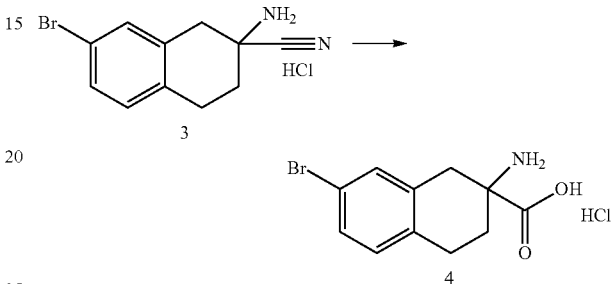

Intermediate 3 (23 g, 80 mmol, 1 eq) was added to 8N hydrochloric acid (200 ml), then was heated to reflux and reacted over night. After the completion of the reaction, the reaction solution was cooled to room temperature, then filtered, and the filter cake was collected and dried to obtain intermediate compound 4 (20 g, 81%) as a yellow solid. MS (M+H$^+$): 271, the theoretical calculating value: 271

Preparation of Intermediate 5:

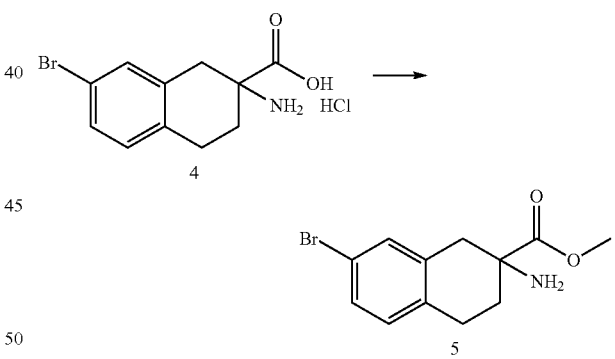

Raw material 4 (20.0 g, 65 mmol, 3.0 eq) was added to the methanol (500 ml), then cooled to 0° C. Thionyl Chloride (23 g, 195 mmol, 3.0 eq) was dropped in the reaction system which was then heated to reflux and reacted for 3 hours. After the reaction completed, the system was concentrated under reduced pressure. Water (300 ml) was added to the resulting residue and saturated sodium bicarbonate was used to regulate the pH (pH=8). The aqueous layer was extracted three times by ethyl acetate (200 ml), and organic layer was combined and washed by aqueous sodium chloride one time, then dried over anhydrous sodium sulfate, and filtered. The mother liquor was concentrated under reduced pressure to give intermediate compound 5 (1.50 g, 81%) as black oil. MS (M+H$^+$): 285, the theoretical calculating value: 285.

Preparation of Intermediate 6:

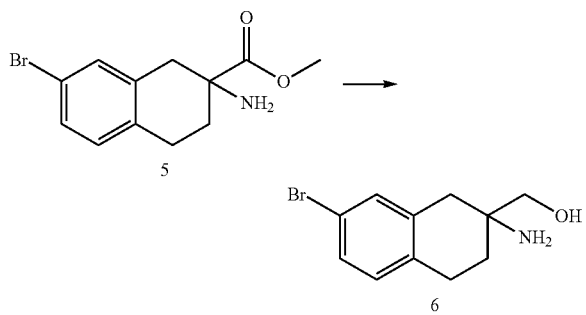

LiAlH$_4$ (4.0 g, 106 mmol, 2.0 eq) was added to tetrahydrofuran (200 ml), and the system was cooled to 0° C. Solution of raw material 5 (15.0 g, 53 mmol, 1.0 eq) in tetrahydrofuran (100 ml) was dropped in, then reacted at 0° C. for 30 minutes. After the completion of the reaction, water (4 ml), and sodium hydroxide (8 ml) were added to the system, and then the mixture was filtered. The mother liquor was concentrated under reduced pressure to obtain intermediate compound 6 (12.0 g, 88%) as black oil. MS (M+H$^+$): 256, the theoretical calculating value: 256.

Preparation of Intermediate 7:

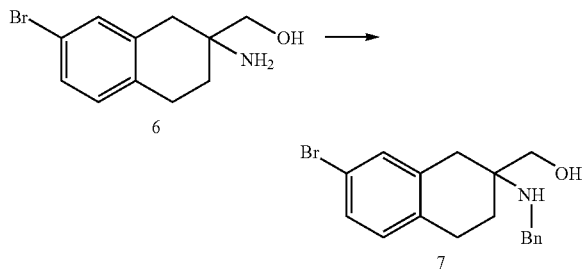

Raw material 6 (13.0 g, 51 mmol, 1.0 eq), acetic acid (4.5 g, 150 mmol, 1.5 eq) and benzaldehyde (5.3 g, 51 mmol, 1.0 eq) were added to dichloromethane (200 ml), and cooled to 0° C. Sodium borohydride acetate (16.0 g, 150 mmol 1.5 eq) was added portionwise, then reacted at 25° C. for 30 minutes. After the completion of the reaction, sodium hydroxide (8 ml) and saturated sodium bicarbonate (100 ml) were added to the system, which was then extracted with dichloromethane (100 ml) for three times. The organic layer was dried over anhydrous sodium sulfate, filtered, and concentrated under reduced pressure to give a crude product, which was purified by silica gel column chromatography (ethyl acetate:heptane=1:10) to obtain intermediate compound 7 (13.0 g, 74%) as brown oil. MS (M+H$^+$): 346, the theoretical calculating value: 346.

Preparation of Intermediate 8:

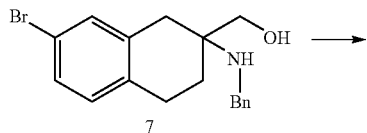

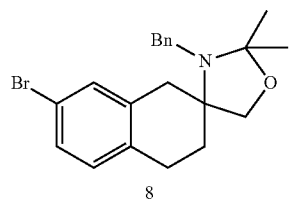

Raw material 7 (13.0 g, 38 mmol, 1.0 eq) and TsOH (0.3 g, cat.) were added to 2,2-dimethoxypropane (100 ml), heated to 120° C. and reacted over night. After the completion of the reaction, the system was concentrated under reduced pressure. Water (100 ml) and saturated sodium bicarbonate (50 ml) were added to the resulting residue, which was then extracted with dichloromethane (100 ml) for three times. The organic layer was dried over anhydrous sodium sulfate, filtered, and concentrated under reduced pressure to give a crude product, which was purified by column chromatography (ethyl acetate:heptane=1:20) to obtain intermediate compound 8 (9.4 g, 65%) as a pale yellow solid. MS (M+H$^+$): 386, 388, the theoretical calculating value: 386, 388.

Preparation of Intermediate 9:

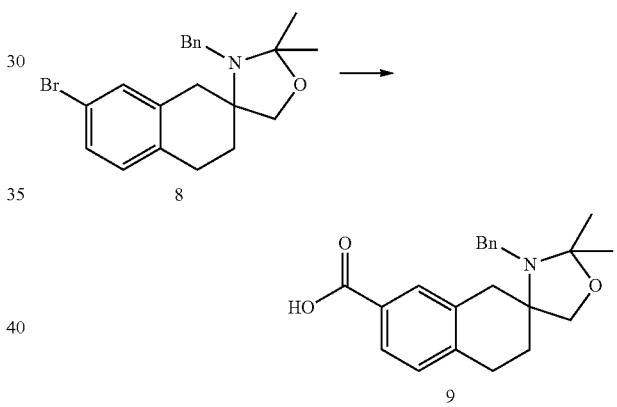

Raw material 8 (5.0 g, 13 mmol, 1.0 eq) was added to tetrahydrofuran (50 ml), and cooled to −78° C. under nitrogen atmosphere. N-BuLi (7.8 ml, 1.5 eq) was added dropwise to the system and the system was reacted at −78° C. for 30 minutes, then dry ice (2 g) was added. After that, the temperature was raised naturally to the room temperature. The system was concentrated under reduced pressure, and water (50 ml) was added to the resulting residue. The pH value was regulated to 4 by 2N HCl, then filtered, and the filter cake was collected and dried to give intermediate compound 9 (4.0 g, 88%) as a white solid. MS (M+H$^+$): 352, the theoretical calculating value: 352.

Preparation of Intermediate 18:

The Reaction Scheme 5: Preparation of Intermediate 18

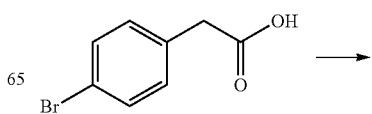

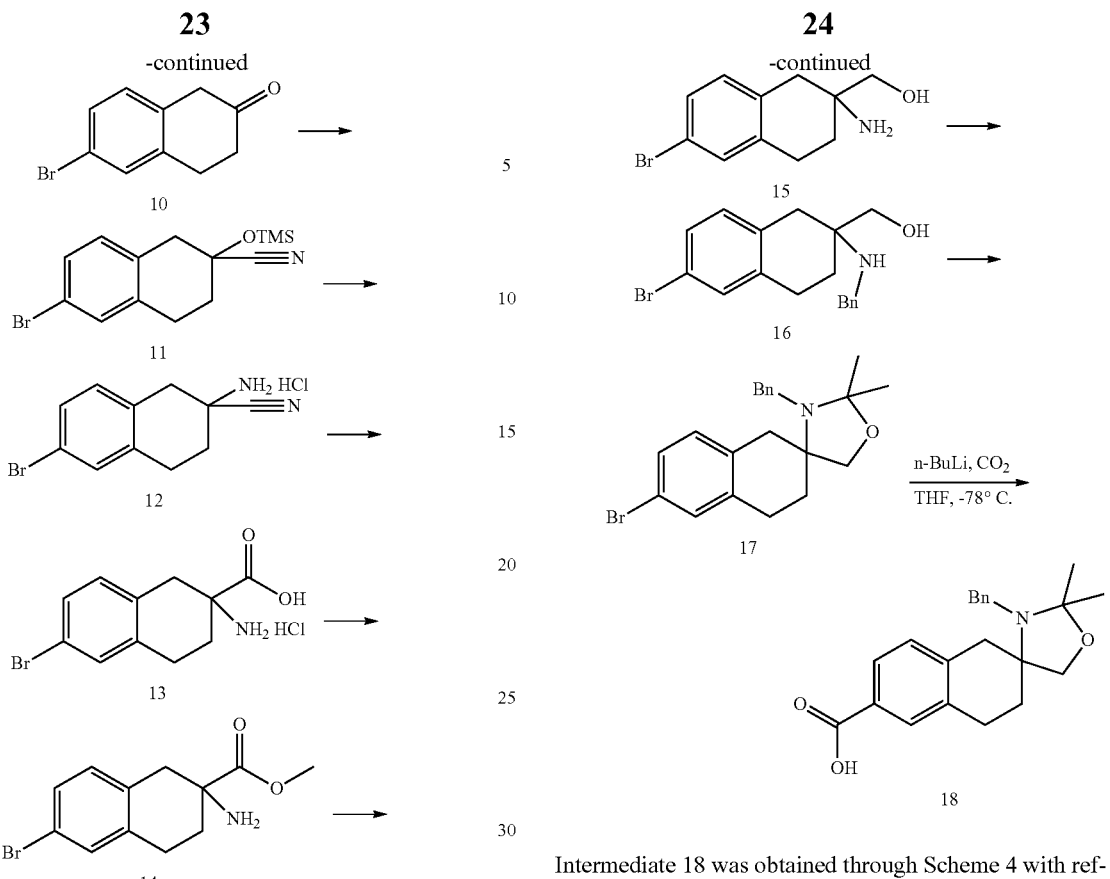
Intermediate 18 was obtained through Scheme 4 with reference to the synthesis method of Intermediate 9.
The Synthesis of Example 1:
The Reaction Scheme 6: The Synthesis of the compound in Example 1
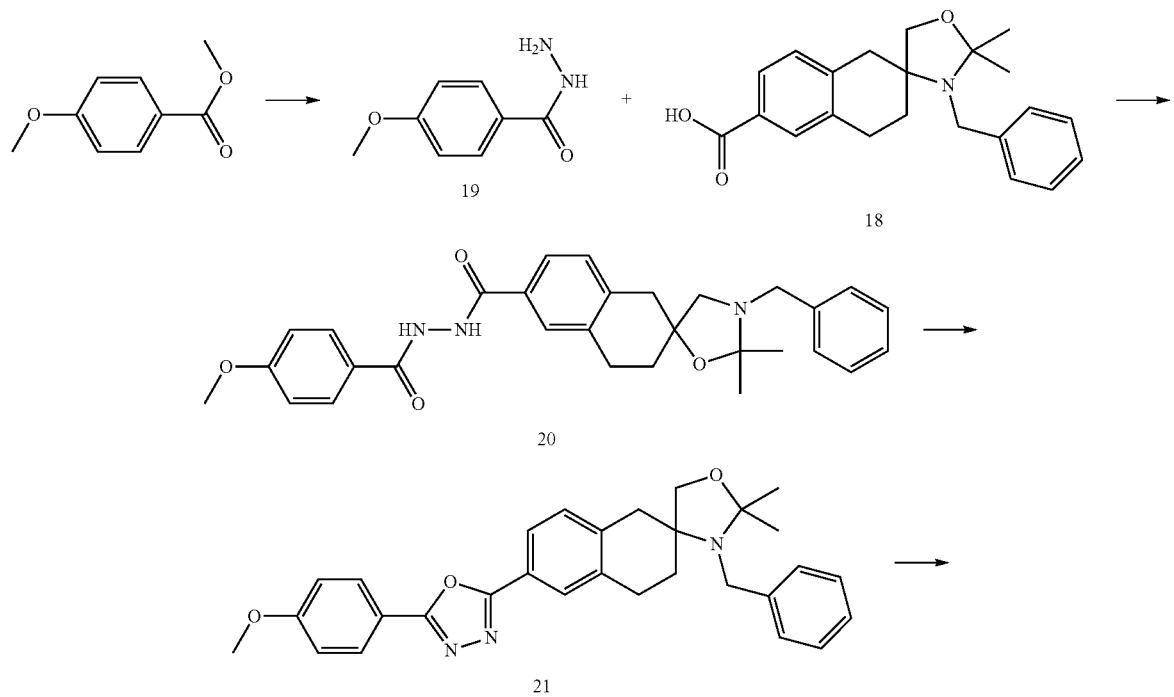

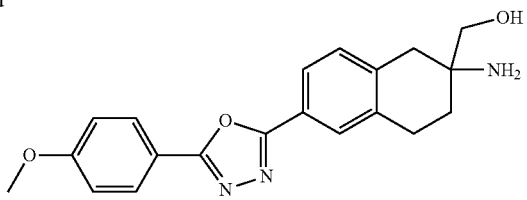

Preparation of Intermediate 19:

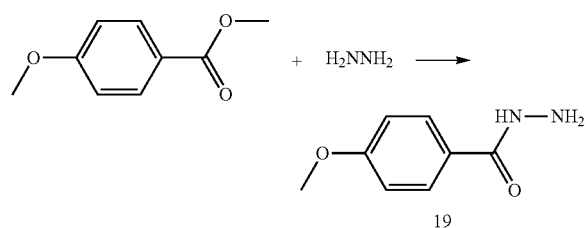

The mixture of 4-methoxy methyl benzoate (33 g, 0.2 mol) and anhydrous hydrazine (7.7 g, 0.24 mmol) was heated to 140° C. under nitrogen atmosphere, and reacted at the said temperature for 30 minutes. After cooled to the room temperature, the mixture was extracted with ethyl acetate (3×100 ml). The organic layer was dried over anhydrous sodium sulfate, and filtered, then concentrated under reduced pressure to give a crude product of intermediate compound 19 (30 g), which can be used for the next reaction step directly.

Preparation of Intermediate 20:

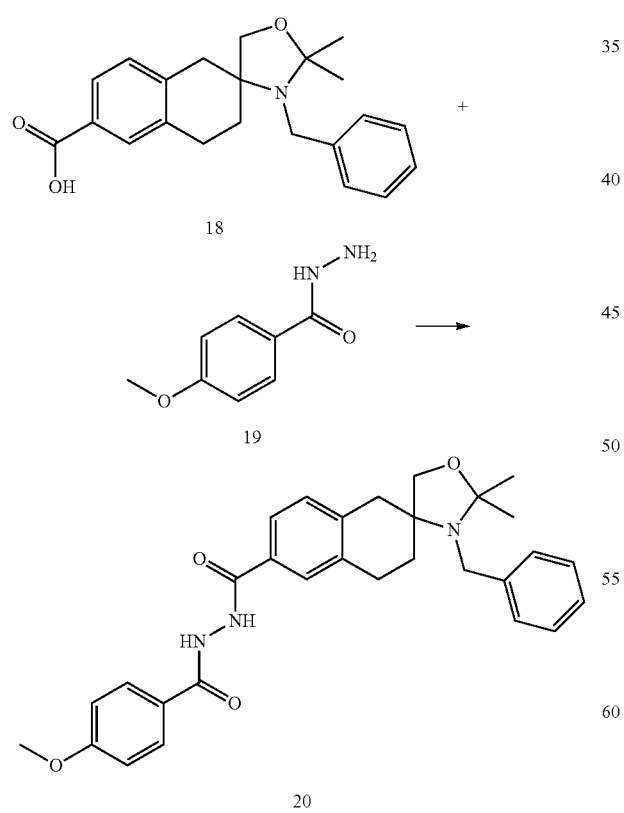

Raw material 18 (0.5 g, 3.0 eq) was dissolved in the dried dichloromethane (20 ml), and DMF (0.01 g, cat.) was added, then the temperature of the system was lowered to 0° C. Oxalyl chloride (500 mg, 3.0 eq) was added dropwise to the system, after which the temperature was raised to room temperature naturally and reacted for 30 minutes. After the completion of the reaction, the system was concentrated under reduced pressure to obtain acyl chloride which was dissolved in dichloromethane (10 ml) for further use.

Compound 19 (240 mg, 1.0 eq) and dichloromethane (20 ml) were added to another reaction flask, and Et₃N (430 mg, 3.0 eq) was added at room temperature, and then cooled to 0° C. The prepared solution of acyl chloride in dichloromethane described above was added dropwise to the system, then heated to room temperature naturally and reacted for 1 h. The reaction was completed under the monitoring of LCMS and Thin-Layer Chromatography (ethyl acetate:petroleum ether=1:1). Water (30 ml) was added to the reaction solution which was then extracted with dichloromethane (3×30 ml). The organic layer was dried and concentrated to give a crude product, which was purified by column chromatography (ethyl acetate:petroleum ether=1:5) to obtain intermediate compound 20 (200 mg).

Preparation of Intermediate 21:

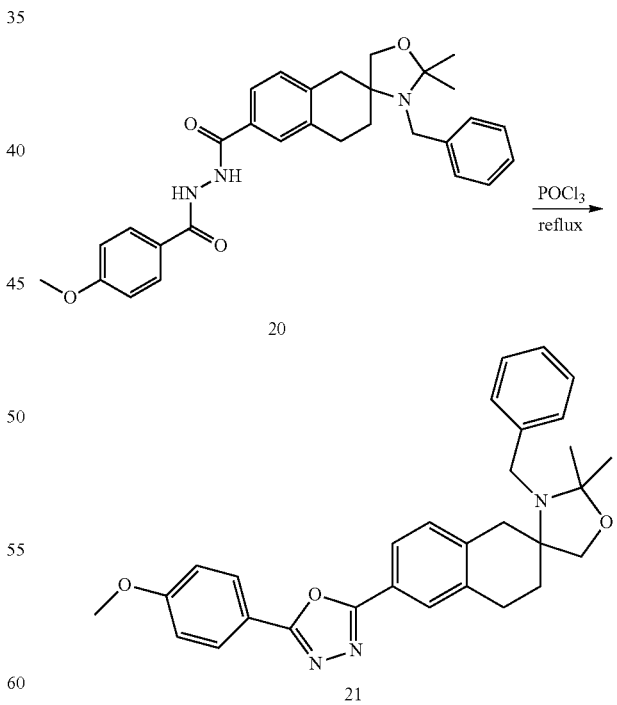

Raw material 20 (1.00 mg, 1.0 eq) was dissolved in POCl₃ (10 ml), then heated to influx, and reacted for 3 hours. The reaction was completed under the monitoring of LCMS and Thin-Layer Chromotography (dichloromethane:methanol-10:1). The reaction solution was concentrated under reduced pressure to gel rid of POCl₃. Ice water (20 g) was added to the resulting residue, and sodium bicarbonate was added to regulate the PH to 8, which was then extracted with dichloromethane (3×30 ml). The organic layer was dried and purified by column chromatography (dichloromethane: methanol=30:1) to obtain intermediate compound 21 (50 mg).

Example 1

6-[5-(4-methoxyphenyl)-2-[1,3,4]oxdiazolyl]-2-amino-1,2,3,4-tetrahydro-naphthalen-2-yl-methanol

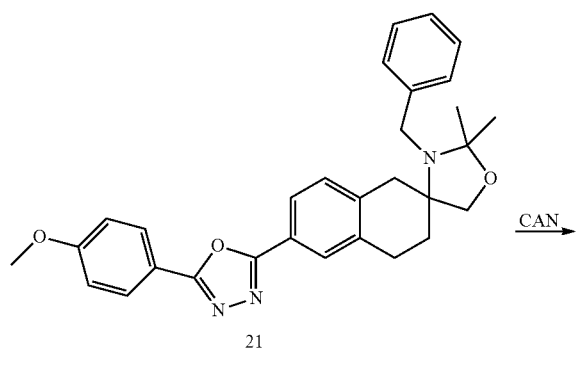

Raw material 21 (45 mg, 0.094 mmol, 1.0 eq) and ammonium eerie nitrate (45 mg) were added to the mixture of acetonitrile (10 ml) and dichloromethane (1 ml). The system was reacted for 5 hours at room temperature, which was under the monitoring of Thin-Layer Chromotography (dichloromethane:methanol=10:1) and LCMS. After the completion of the reaction, water (20 ml) was added to the system, which was then extracted with dichloromethane (3×20 ml). The organic layer was combined and washed with saturated aqueous sodium chloride solution (20 ml), dried over anhydrous sodium sulfate, filtered, and concentrated under reduced pressure to give a crude product, which was purified by column chromatography (dichloromethane:methanol=50:1) to obtain the compound in Example 1 (20 mg, 61%) as a white solid. NMR (400 MHz, CDCl₃) δ=7.42 (2H, d), 7.32 (2H, d), 7.21 (2H, m), 6.90 (1H, d), 3.86 (3H, s), 3.70 (2H, dd), 2.80 (4H, m), 1.82 (2H, m); Rt=3.12 min, MS (M+H⁺): 352, the theoretical calculating value: 352.

The compounds in the following examples were obtained by synthesis method similar as that used in Example 1:

Example 2

6-[5-(4-ethoxyphenyl)-2-[1,3,4]-oxdiazolyl]-2-amino-1,2,3,4-tetrahydro-naphthalen-2-yl-methanol

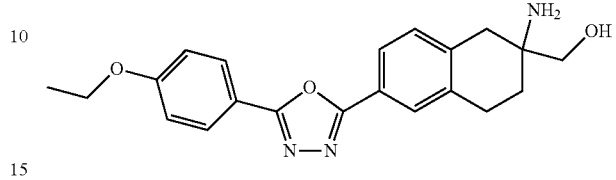

NMR (400 MHz, CD₃OD) δ=8.04 (2H, d), 7.92 (2H, m), 7.41 (1H, m), 7.52 (2H, d), 4.10 (2H, m), 3.60 (2H, d), 3.30 (4H, m), 3.00 (2H, m), 1.40 (3H, t); Rt=3.34 min, MS (M+H⁺): 366, the theoretical calculating value: 366.

Example 3

6-[5-(4-fluorophenyl)-2-[1,3,4]oxdiazolyl]-2-amino-1,2,3,4-tetrahydro-naphthalen-2-yl-methanol

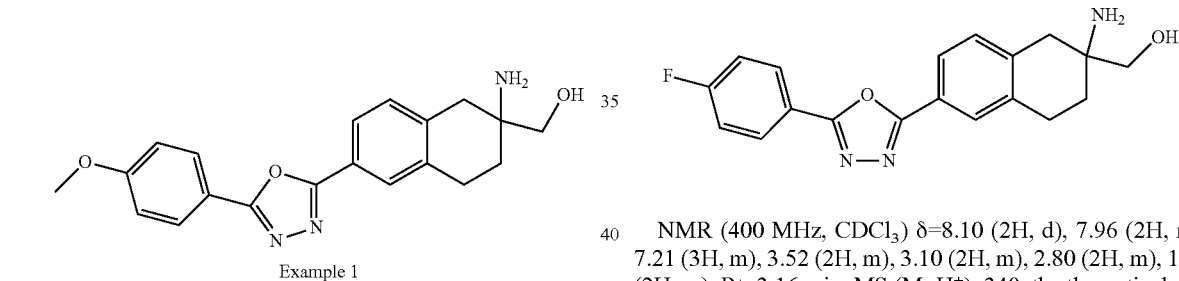

NMR (400 MHz, CDCl₃) δ=8.10 (2H, d), 7.96 (2H, m), 7.21 (3H, m), 3.52 (2H, m), 3.10 (2H, m), 2.80 (2H, m), 1.82 (2H, m), Rt=3.16 min, MS (M+H⁺): 340, the theoretical calculating value: 340.

Example 4

6-[5-(3-fluorophenyl)-2-[1,3,4]oxdiazolyl]-2-amino-1,2,3,4-tetrahydro-naphthalen-2-yl-methanol

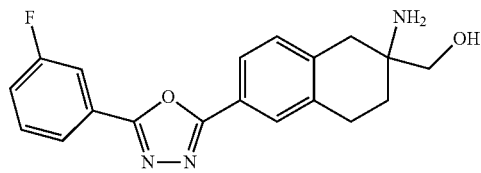 [SMILES: NC1(CO)CCc2cc(-c3nnc(-c4cccc(F)c4)o3)ccc2C1]

NMR (400 MHz, CDCl₃) δ=8.00 (1H, m), 7.90 (1H, m), 7.64 (1H, m), 7.22 (3H, m), 3.52 (2H, m), 3.10 (2H, m), 2.80 (2H, m), 1.82 (2H, m); Rt=3.24 min, MS (M+H⁺): 340, the theoretical calculating value: 340.

Example 5

6-[5-(2-fluorophenyl)-2-[1,3,4]oxdiazolyl]-2-amino-1,2,3,4-tetrahydro-naphthalen-2-yl-methanol

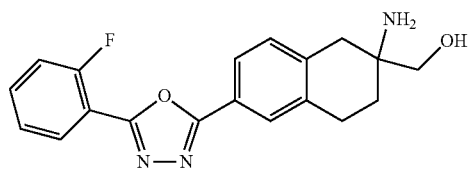 [SMILES: NC1(CO)CCc2cc(-c3nnc(-c4ccccc4F)o3)ccc2C1]

NMR (400 MHz, CD$_3$OD) δ=8.16 (1H, m), 7.92 (2H, m), 7.64 (1H, m), 7.32 (3H, m), 3.62 (2H, m), 3.10 (2H, m), 2.42 (2H, m), 1.64 (2H, m); Rt=3.10 min, MS (M+H$^+$): 340, the theoretical calculating value: 340.

Example 6

6-[5-(4-pyridyl)-2-[1,3,4]oxdiazolyl]-2-amino-1,2,3,4-tetrahydro-naphthalen-2-yl-methanol

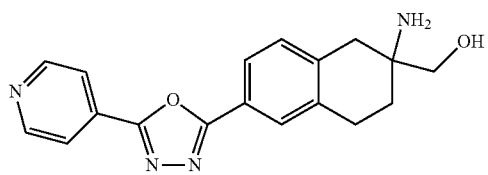 [SMILES: NC1(CO)CCc2cc(-c3nnc(-c4ccncc4)o3)ccc2C1]

NMR (400 MHz, CD$_3$OD) δ=8.70 (2H, d), 8.20 (2H, 2), 7.64 (1H, m), 7.30 (3H, m), 3.60 (2H, m), 3.00 (2H, m), 2.02 (2H, m), 1.24 (2H, m); Rt=2.77 min, MS (M+H$^+$): 323, the theoretical calculating value: 323.

Example 7

6-[5-(4-piperidyl)-2-[1,3,4]oxdiazolyl]-2-amino-1,2,3,4-tetrahydro-naphthalen-2-yl-methanol

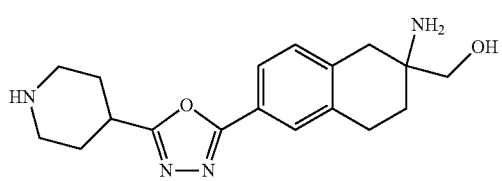 [SMILES: NC1(CO)CCc2cc(-c3nnc(C4CCNCC4)o3)ccc2C1]

NMR (400 MHz, CD$_3$OD) δ=7.64 (2H, m), 7.30 (1H, m), 3.60 (2H, m), 3.00 (2H, m), 2.82 (4H, m), 2.64 (1H, m), 2.02 (2H, m), 1.80 (4H, m), 1.24 (2H, m); Rt=2.40 min, MS (M+H$^+$): 329, the theoretical calculating value: 329.

Example 8

1-{4-[5-(6-hydroxymethyl-6-amino-5,6,7,8-tetrahydro-naphthalen-2-yl)-2-[1,3,4]oxdiazolyl]-1-piperidyl}ethanone

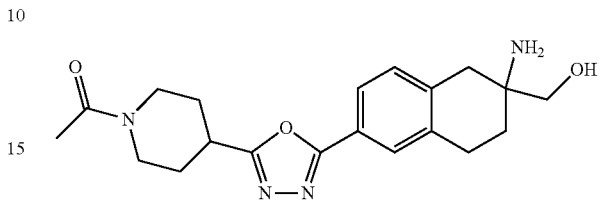

NMR (400 MHz, CDCl$_3$) δ=7.80 (2H, m), 7.20 (1H, m), 3.76 (2H, m), 3.60 (4H, m), 3.10 (2H, m), 2.82 (2H, m), 2.64 (1H, m), 2.24 (3H, s), 2.02 (2H, m), 1.80 (4H, m), 1.24 (2H, m); Rt=2.64 min, MS (M+H$^+$): 371, the theoretical calculating value: 371.

Example 9

6-[5-(3-methyl-4-methoxy phenyl)-2-[1,3,4]oxdiazolyl]-2-amino-1,2,3,4-tetrahydro-naphthalen-2-yl-methanol

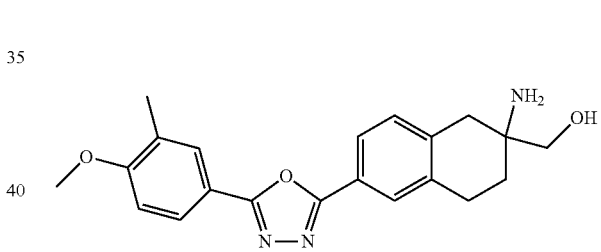

NMR (400 MHz, CDCl$_3$) δ=7.94 (1H, m), 7.90 (2H, m), 7.82 (1H, m), 7.20 (1H, m), 6.66 (1H, d), 3.90 (3H, s), 3.70 (2H, dd), 2.90 (4H, m), 2.30 (3H, s), 1.52 (2H, m); Rt=3.38 min, MS (M+H$^+$): 366, the theoretical calculating value: 366.

Example 10

7-{5-[4-(2-methoxyethoxy)phenyl]-2-[1,3,4]oxdiazolyl]-2-amino-1,2,3,4-tetrahydro-naphthalen-2-yl-methanol

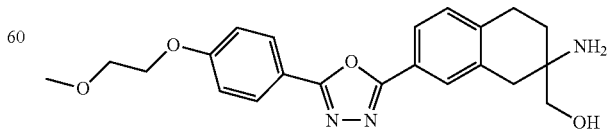

NMR (400 MHz, DMSO-d$_6$) δ=8.05 (2H, d), 7.85 (2H, m), 7.35 (1H, m), 7.15 (2H, d), 4.20 (2H, m), 3.62 (2H, m), 3.30

(3H, s), 2.90 (4H, m), 1.85 (2H, m); Rt=3.21 min, MS (M+H+): 396, the theoretical calculating value: 396.

Example 11

7-[5-(3-trifluoromethyl-4-isopropoxyphenyl)-2-[1,3,4]oxdiazolyl]-2-amino-1,2,3,4-tetrahydronaphthalen-2-yl-methanol

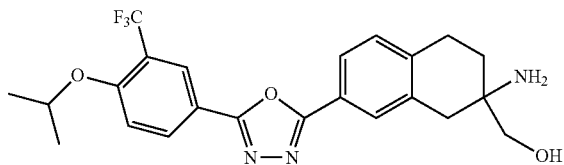 [SMILES: CC(C)Oc1ccc(-c2nnc(-c3ccc4c(c3)CC(N)(CO)CC4)o2)cc1C(F)(F)F]

NMR (400 MHz, CD$_3$Cl$_3$) δ=7.9 (2H, m), 7.60 (1H, m), 7.35 (1H, m), 7.00 (1H, m), 6.85 (1H, m), 4.60 (1H, m), 3.75 (2H, m), 3.150 (2H, m), 2.70 (2H, m), 2.10 (2H, m), 1.32 (6H, d), Rt=3.90 min, MS (M+H+): 448, the theoretical calculating value: 448.

Example 12

6-[5-(3-nitro-4-pyridyl)-3-1,2,4-oxdiazolyl]-2-amino-1,2,3,4-tetrahydro-naphthalen-2-yl-methanol

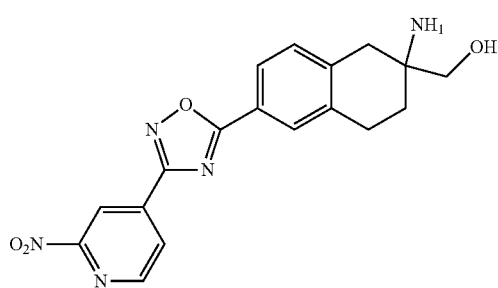 [SMILES: NC1(CO)CCc2cc(-c3nc(-c4ccnc([N+](=O)[O-])c4)no3)ccc2C1]

NMR (400 MHz, DMSO-d$_6$) δ=8.95 (1H, m), 8.82 (1H, m), 8.50 (1H, m), 7.91 (2H, m), 7.38 (1H, m), 5.02 (1H, d), 2.90 (4H, m), 2.70 (2H, d), 1.78 (2H, m), Rt=3.04 min, MS (M+H+): 368, the theoretical calculating value: 368.

Example 13

7-[5-(2-hydroxymethyl-4-pyridyl)-2-[1,3,4]-oxdiazolyl]-2-amino-1,2,3,4-tetrahydronaphthalen-2-yl-methanol

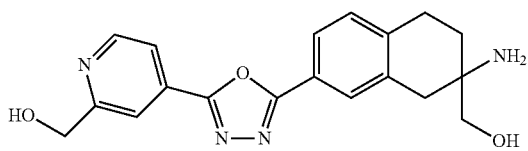 [SMILES: NC1(CO)CCc2ccc(-c3nnc(-c4ccnc(CO)c4)o3)cc2C1]

NMR (400 MHz, CD$_3$Cl$_3$) δ=7.72 (1H, m), 7.50 (1H, m), 7.41 (2H, m), 7.01 (1H, m), 6.80 (1H, m), 5.12 (2H, d), 4.10 (2H, d), 3.60 (2H, d), 3.30 (2H, m), 1.82 (2H, m), Rt=2.71 min, MS (M+H+): 353, the theoretical calculating value: 353.

Example 14

4-[5-(7-hydroxymethyl-7-amino-5,6,7,8-tetrahydronaphthalen-2-yl)-1,3,4-oxdiazolyl]-1-indenol

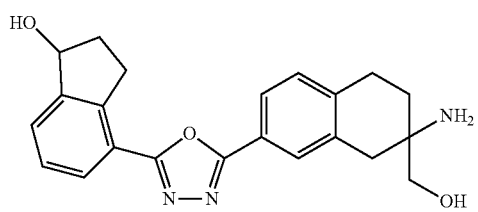 [SMILES: NC1(CO)CCc2ccc(-c3nnc(-c4cccc5c4CCC5O)o3)cc2C1]

NMR (400 MHz, DMSO-d$_6$) δ=8.05 (1H, d), 7.85 (2H, m), 7.60 (1H, d), 7.50 (1H, m), 7.35 (1H, m), 5.45 (1H, m), 5.15 (1H, m), 3.5 (2H, m), 3.20 (2H, m), 3.00 (2H, m) 2.70 (4H, m), 1.90 (2H, m); Rt=2.97 min, MS (M+H+); 378, the theoretical calculating value: 378.

Example 15

7-[5-(4-methoxy-3-methyl phenyl)-2-1,3,4-oxdiazolyl]-2-amino-1,2,3,4-tetrahydro-naphthalen-2-yl-methanol

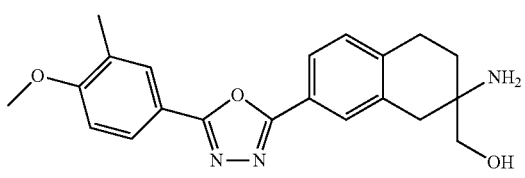 [SMILES: COc1ccc(-c2nnc(-c3ccc4c(c3)CC(N)(CO)CC4)o2)cc1C]

NMR (400 MHz, DMSO-d$_6$) δ=7.95 (3H, m), 7.85 (1H, s), 7.36 (1H, s), 7.14 (1H, d), 3.90 (3H, s), 2.90 (4H, m), 2.85 (2H, m), 2.25 (3H, s), 1.88 (2H, m), Rt=3.49 min, MS (M+H+): 366, the theoretical calculating value: 366.

Example 16

7-[5-(4-isopropoxyphenyl)-2-1,3,4-oxdiazolyl]-2-amino-1,2,3,4-tetrahydro-naphthalen-2-yl-methanol

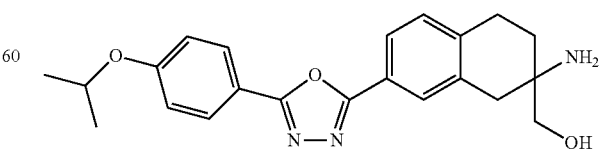

NMR (400 MHz, DMSO-d$_6$+D$_2$O) δ=8.10 (2H, d), 7.90 (2H, d), 7.41 (1H, d), 7.20 (2H, d), 4.81 (1H, m), 3.45 (2H, m),

Example 17

7-{5-[4-(2-methoxyethoxy)-3-trifluoromethyl phenyl]-2-1,3,4-oxdiazolyl}-2-amino-1,2,3,4-tetrahydro-naphthalen-2-yl-methanol

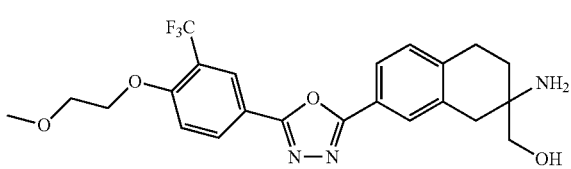 [SMILES: COCCOc1ccc(-c2nnc(-c3ccc4c(c3)CC(N)(CO)CC4)o2)cc1C(F)(F)F]

NMR (400 MHz, DMSO+$D_2O$) δ=8.37 (1H, d), 8.27 (1H, s), 7.87 (2H, m), 7.54 (1H, d), 7.35 (1H, d), 4.38 (2H, m), 3.74 (2H, m), 3.33 (5H, m), 2.90 (2H, m), 2.83 (2H, m), 1.86 (2H, m), Rt=3.64 min, MS (M+H$^+$): 464, the theoretical calculating value: 464.

Example 18

7-{5-[4-(2-methoxyethoxy)-3-methyl phenyl]-2-1,3,4-oxdiazolyl}-2-amino-1,2,3,4-tetrahydro-naphthalen-2-yl-methanol

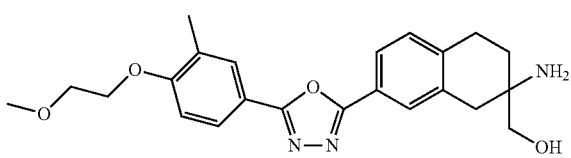 [SMILES: COCCOc1ccc(-c2nnc(-c3ccc4c(c3)CC(N)(CO)CC4)o2)cc1C]

NMR (400 MHz, DMSO-$d_6$) δ7.95 (2H, d), 7.83 (2H, d), 7.34 (1H, d), 7.15 (1H, d), 4.22 (2H, s), 3.74 (2H, m), 3.44 (2H, m), 3.33 (3H, s), 2.95 (2H, m), 2.83 (2H, m), 2.26 (3H, s), 1.83 (2H, m); Rt=3.07 min, MS (M+H$^+$): 410, the theoretical calculating value: 410.

Example 19

7-[5-(6-isopropoxy-3-pyridyl)-2-[1,3,4]-oxdiazolyl]-2-amino-1,2,3,4-tetrahydronaphthalen-2-yl-methanol

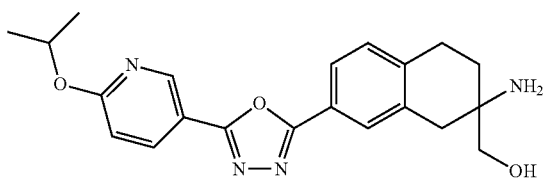 [SMILES: CC(C)Oc1ccc(-c2nnc(-c3ccc4c(c3)CC(N)(CO)CC4)o2)cn1]

NMR (400 MHz, CDCl$_3$) δ=8.85 (1H, s), 8.22 (1H, d), 7.81 (2H, d), 7.22 (1H, d), 6.80 (1H, d), 5.39 (1H, m), 3.54 (2H, s), 3.00 (2H, m), 2.89 (2H, m), 1.88 (2H, m), 1.39 (3H, s), 1.37 (3H, s); Rt=3.68 min, MS (M+H$^+$): 381, the theoretical calculating value: 381.

Example 20

7-[5-(3,4-diethoxyphenyl)-2-[1,3,4]-oxdiazolyl]-2-amino-1,2,3,4-tetrahydro-naphthalen-2-yl-methanol

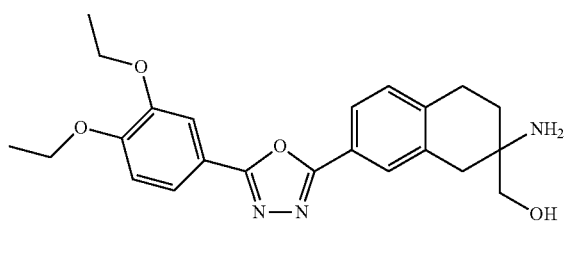 [SMILES: CCOc1ccc(-c2nnc(-c3ccc4c(c3)CC(N)(CO)CC4)o2)cc1OCC]

LC-MS: 410.2 [M+1]$^+$, $t_R$=1.822 min. $^1$H NMR (400 MHz, DMSO) δ 7.90-7.77 (m, 2H), 7.68 (dd, J=8.4, 1.9 Hz, 1H), 7.59 (d, J=1.9 Hz, 1H), 7.33 (d, J=7.9 Hz, 1H), 7.17 (d, J=8.5 Hz, 1H), 4.98 (br s, 1H), 4.14 (p, J=6.8 Hz, 4H), 3.29 (s, 2H), 3.04-2.60 (m, 4H), 1.83-1.59 (m, 2H), 1.41-1.33 (m, 6H).

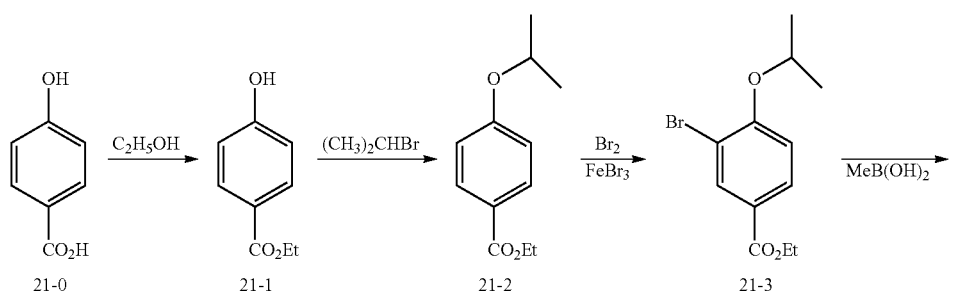

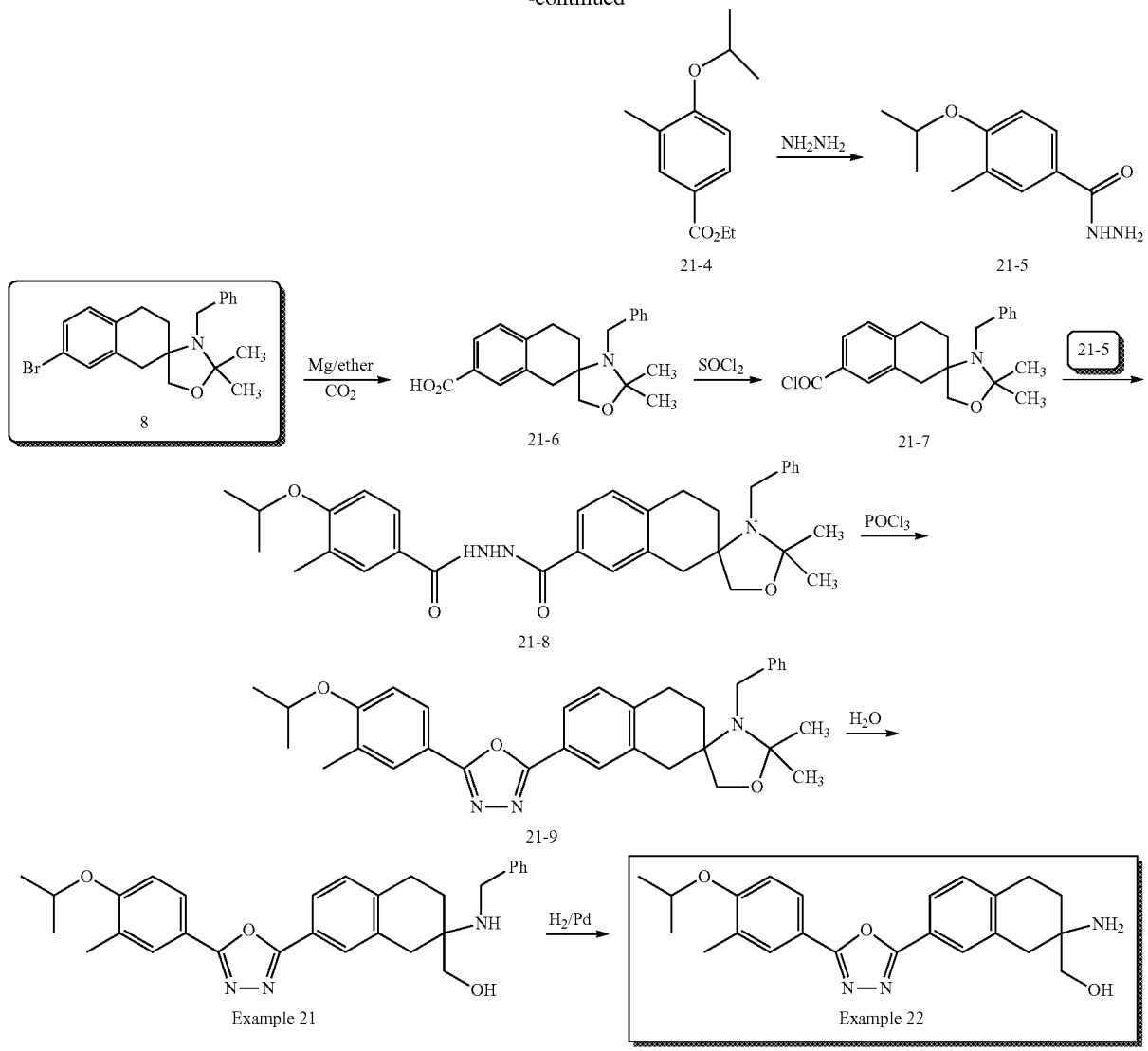

The Synthesis of Intermediate 21-1

The compound 21-0 (4-hydroxyl benzoic acid) (5 g, 36 mmol) and anhydrous ethanol (50 mL) were heated to reflux. Sulfuric acid (3.4 mL, 63 mmol) was added slowly dropwise to the system, and then the reaction solution was stirred and reacted for 8 hours. After the removal of most ethanol, the reaction solution was left to precipitate, and then filtered. The filter cake was washed with water until neutral and dried to obtain compound 21-1 (5 g, 83% yield) as a white solid; mp 109-111° C.; $^1$H NMR (400 MHz, CDCl$_3$) δ: 7.92 (d, 2H, J=8.4 Hz, 2×—ArH), 6.88 (d, 2H, J=8.0 Hz, 2×—ArH), 5.97 (s, 1H, —OH), 4.38 (q, 2H, J=6.8 Hz, —CH$_2$—) 1.38 (t, 3H, J=6.8 Hz, —CH$_3$); $^{13}$C NMR (100 MHz, CDCl$_3$) δ: 167.4, 160.6, 131.9, 131.9, 122.1, 115.3, 115.3, 61.1, 14.2.

The Synthesis of the Intermediate 21-2

The compound 21-1 (16 g, 76.9 mmol), anhydrous potassium carbonate (39.8 g, 0.29 mol) and anhydrous ethyl alcohol (200 mL) were heated to 60° C. The solution of 2-bromo propane (35.5 g, 0.29 mol) in anhydrous ethyl alcohol (50 ml) was added dropwise to the system, and was stirred and reacted for 2 hours maintaining 60° C. After the reaction completed, the solvent was removed and the resulting residue was purified by silica gel column chromatography (developing solvent: ethyl acetate:petroleum ether=1:10) to obtain compound 21-2 (20 g, 99% yield) as colorless oil; $^1$H NMR (400 MHz, CDCl$_3$) δ: 7.97 (d, 2H, J=8.0 Hz, 2×—ArH), 6.88 (d, 2H, J=8.0 Hz, 2×—ArH), 4.62 (t, 1H, J=5.6 Hz, —CH—), 4.33 (d, 2H. J=6.8 Hz, —CH$_2$—), 1.34 (d, 9H, J=4.8 Hz, 3×—CH$_3$), $^{13}$C NMR (100 MHz, CDCl$_3$) δ: 166.3, 161.6, 131.4, 131.4, 122.4, 114.9, 114.9, 69.9, 60.4, 21.8, 14.3.

The Synthesis of the Intermediate 21-3

The compound 21-2 (2 g, 12 mmol) and dichloromethane 50 ml were cooled to −10° C. in ice-salt bath. Maintaining −10° C., the solution of bromine (1.53 g, 1.2 mmol) in dichloromethane (20 ml) was added slowly dropwise to the system. Then, the reaction solution was stirred and reacted for 3.5 hours at 40° C. The solution of 10% sodium thiosulphate was added and the system was stirred to colorless. The aqueous layer was extracted with dichloromethane for three times. Organic layer was dried over anhydrous magnesium sulfate, and then filtered, concentrated and purified by silica gel column chromatography (developing solvent: ethyl acetate:petroleum ether=1:3) to obtain compound 21-3 (1.8 g, 65% yield) as colorless oil; $^1$H NMR (400 MHz, CDCl$_3$) δ: 8.13 (s, 1H, —ArH), 7.85 (d, 1H, J=8.8 Hz, —ArH), 6.80 (d, 1H, J=8.8, Hz, —ArH), 4.56-4.53 (m, 1H, —CH—), 4.28 (q, 2H, J=7.2 Hz, —CH$_2$), 1.29 (t, 9H, J=6.8 Hz, 3×—CH$_3$); $^{13}$C NMR (100 MHz, CDCl$_3$) δ: 164.7, 157.8, 134.5, 129.9, 123.5, 113.0, 112.4, 71.6, 60.5, 21.5, 14.0.

The Synthesis of the Intermediate 2.1-4

The compound 21-3 (1.5 g, 5 mmol), methylboronic acid (0.34 g, 5.5 mmol), K$_3$PO$_4$.3H$_2$O (4.15 g, 15 mmol), tetrakis (triphenylphosphine)palladium (0.13 g, 0.25 mmol), and toluene (30 ml) were heated to reflux under nitrogen atmosphere and reacted for 3 hours. The reaction was quenched with water. The solution was extracted with ethyl acetate for three times. Organic layer was dried over anhydrous magnesium sulfate, filtered, concentrated and purified by silica gel column chromatography (developing solvent: ethyl acetate: petroleum ether=1:50) to obtain compound 21-4 (0.75 g, 65% yield) as colorless oil; $^1$H NMR (400 MHz, CDCl$_3$) δ: 7.86-7.83 (m, 2H, 2×—ArH), 6.82 (d, 1H, J=8.4 Hz, —ArH), 4.62-4.59 (m, 1H, —CH—), 4.35 (q, 2H, J=7.2 Hz, —CH2-), 2.13 (s, 3H, Ar—CH$_3$), 1.38-1.34 (m, 9H, 3×—CH$_3$); $^{13}$C NMR (100 MHz, CDCl$_3$) δ: 166.6, 159.9, 132.0, 128.9, 127.3, 121.8, 111.2, 70.0, 60.3, 22.0, 16.2, 14.3.

The Synthesis of the Intermediate 2.1-5

The compound 21-4 (5 g, 22 mmol), hydrazine hydrate (80%, 13.6 mL, 0.22 mol), and anhydrous ethyl alcohol (80 mL), were heated to reflux and reacted overnight. After the solvent was evaporated, the resulting residue was purified by silica gel column chromatography (developing solvent: ethyl acetate) to obtain compound 21-5 (4.5 g, 95% yield) as a white solid; mp 97-99° C.; $^1$H NMR (400 MHz, CDCl$_3$) δ: 8.69 (s, 1H, —NH—), 7.57 (s, 2H, 2×—ArH), 6.70 (d, 1H, J=8.4 Hz, —ArH), 4.48 (t, 1H, J=6.0 Hz, —CH—), 4.22 (s, 2H, —NH$_2$), 2.09 (s, 3H, Ar—CH$_3$), 1.26 (d, 6H, J=5.6 Hz, 2×—CH$_3$); $^{13}$C NMR (100 MHz, CDCl$_3$) δ: 168.3, 158.7, 129.5, 127.3, 125.9, 123.7, 111.3, 69.8, 21.8, 21.6, 16.1.

The Synthesis of the Intermediate 21-6

Under nitrogen atmosphere, Mg (0.78 g, 28.6 mmol), and a few grains of iodine were added and heated to 80° C. A small amount of solution of the intermediate 8 (3-benzyl-4-[7-bromo-1,2,3,4-tetrahydronaphthyl]-2,2-dimethyl-1,3-oxazolidine) (10 g, 26 mmol) in THF (1.00 mL) was added dropwise to initiate the reaction. The remainder of the intermediate 8 solution was continuously added dropwise to the reaction solution while stirring and maintaining the reaction system micro-boiling. After that, the reflux reaction continued for 5 hours. The reaction system was then cooled, and maintained the reaction temperature at −10° C. Dry CO$_2$ was passed in for 1.5 hours, and concentrated sulfuric acid (1.4 mL) was added dropwise at 0° C., and then continued stirring for 0.5 hours. After evaporation of solvent, the resulting residue was purified by silica gel column chromatography (developing solvent: ethyl acetate:petroleum ether=1:3) to obtain compound 21-6 (5.3 g, 58% yield) as a white solid; mp 180-182° C.; $^1$H NMR (400 MHz, DMSO) δ: 12.71 (s, 1H, —CO$_2$H), 7.65 (d, 2H, J=8.4 Hz, 2×—ArH), 7.40 (d, 2H, J=7.2 Hz, 2×—ArH), 7.28 (t, 2H, J=7.6 Hz, 2×—ArH), 7.21-7.14 (m, 2H, 2×—ArH), 3.87 (s, 2H, —CH$_2$—), 3.65 (d, 1H, J=8.0 Hz, —CH$_2$.OH), 3.50 (d, 1H, J=8.0 Hz, —CH$_2$—OH), 2.91 (t, 2H, J=16.8 Hz, —CH$_2$—), 2.77 (t, 2H, J=16.0 Hz, —CH$_2$—), 1.82-1.74 (m, 2H, —CH$_2$—), 1.22 (s, 3H, —CH$_3$), 1.08 (s, 3H, —CH$_3$); $^{13}$C NMR (100 MHz, DMSO) δ: 167.3, 141.4, 140.7, 136.3, 130.3, 128.5, 128.2, 127.9, 127.9, 126.6, 126.6, 126.5, 94.8, 71.9, 62.0, 45.8, 35.9, 30.2, 27.6, 27.3, 27.0.

The Synthesis of the Intermediate 21-8

The intermediate 21-6 (2 g, 5.7 mmol), dichloridemethane 40 mL, and thionyl chloride (1.24 mL, 17.1 mmol) were heated to reflux and reacted for 3 hours. After solvent was evaporated, the crude product acyl chloride 21-7 was obtained, which was directly used in the next reaction without purification. The intermediate 21-5 (1.2 g, 5.8 mmol), THF 30 mL, and pyridine (0.9 mL, 11.5 mmol) were bathed in ice-salt at −5° C., then a solution of crude acyl chloride 21-7 in THF (20 mL) was added dropwise in the mixture. After adding, the system was continued stirred for 0.5 h, and then a little water was added to quench the reaction. The reaction solution was extracted with ethyl acetate for three times, and the organic layer was dried over anhydrous magnesium sulfate and filtered. Then the filtrate was evaporated and purified by silica gel column chromatography (developing solvent: ethyl acetate:dichloromethane=1:15) to obtain compound 21-8 as a pale yellow solid (1.4 g, 45% yield); mp 116-117° C. $^1$H NMR (400 MHz, CDCl$_3$) δ: 9.90 (d, 1H, J=5.2 Hz, —CONH—), 9.85 (d, 1H, J=4.4 Hz, —CONH—), 7.73 (d, 1H, J=8.4 Hz, —ArH), 7.67 (s, 1H, —ArH), 7.60 (d, 2H, J=6.6 Hz, 2×—ArH), 7.39 (d, 2H, J=7.2 Hz, 2×—ArH), 7.28 (t, 2H, J=6.8 Hz, 2×—ArH), 7.21 (d, 1H, J=7.2 Hz, —ArH), 7.11 (d, 1H, J=8.4 Hz, —ArH), 6.77 (d, 1H, J=8.4 Hz, —ArH), 4.58-4.55 (m, 1H, —CH—), 3.83 (s, 2H, —CH$_2$—), 3.83-3.61 (m, 2H, —CH$_2$—), 2.88-2.75 (m, 4H, 2×—CH$_2$—), 2.15 (s, 3H, —CH$_3$), 1.82-1.80 (m, 2H, —CH$_2$—), 1.34-1.27 (m, 6H, 2×—CH$_3$), 1.27 (s, 3H, —CH$_3$), 1.18 (s, 3H, —CH$_3$); $^{13}$C NMR (100 MHz, CDCl$_3$) δ: 165.5, 165.4, 159.3, 141.1, 139.9, 136.4, 130.2, 128.9, 128.8, 128.5, 128.3, 128.3, 127.9, 127.9, 127.4, 126.9, 126.6, 124.7, 122.5, 111.3, 95.4, 72.5, 69.9, 62.3, 46.4, 36.0, 30.8, 28.1, 27.6, 27.0, 21.9, 16.2.

The Synthesis of the Intermediate 21-9

Under the nitrogen atmosphere, compound 21-8 1.2 g (2.2 mmol) and POCl$_3$ (20 mL) were heated to 100° C. and stirred for 3 hours. After evaporation of solvent, the resulting residue was purified by silica gel column chromatography (methanol:dichloromethane=3:30) to obtain compound 21-9 (0.2 g, 45% yield); mp 280-282° C.; $^1$H NMR (400 MHz, CDCl$_3$) δ: 7.92 (d, 2H, J=6.8 Hz, 2×—ArH), 7.82 (t, 2H, J=8.0 Hz, 2×—ArH), 7.42 (d, 2H, J=7.2 Hz, 2×—ArH), 7.30 (t, 2H, J=7.2 Hz, 2×—ArH), 7.20 (t, 2H, J=8.0 Hz, 2×—ArH), 6.93 (d, 1H, J=8.0 Hz, —ArH), 4.66-4.63 (m, 1H, —CH—), 3.90 (s, 2H, —CH$_2$—), 3.80-3.70 (m, 2H, —CH$_2$—), 3.03-2.88 (m, 4H, 2×—CH$_2$—), 2.28 (s, 3H, —CH$_3$), 1.96-1.89 (m, 2H, —CH$_2$—), 1.40-1.36 (m, 6H, 2×—CH$_3$), 1.25 (s, 3H, —CH$_3$), 1.21 (s, 3H, —CH$_3$); $^{13}$C NMR (100 MHz, CDCl$_3$) δ: 164.5, 164.0, 158.9, 141.1, 139.4, 137.1, 129.3, 129.1, 128.4, 128.3, 128.0, 127.8, 126.8, 126.0, 124.1, 121.6, 115.4, 112.1, 95.5, 72.7, 70.2, 62.4, 46.5, 36.4, 30.7, 28.2, 27.5, 27.2, 22.0, 16.3.

Example 21

2-(7-benzylamino-5,6,7,8-tetrahydro-7-naphthalenemethanol)-5-(3-methyl-4-isopropoxy)-1,3,4-oxdiazole (Compound 179 in Prior Patent Application of 201110155280.X)

Under nitrogen atmosphere, compound 21-9 1.2 g (2.2 mmol), p-TsOH 0.02 g (0.013 mmol) and methanol 50 mL were heated to reflux and reacted. After rotary evaporation of solvent, the resulting residue was purified by column chromatography (developing solvent: methanol:dichloromethane=1:50) to obtain the compound in Example 22 as a white solid (0.4 g, 60% yield), mp 159-161° C.; $^1$H NMR (300 MHz, CDCl$_3$) δ: 7.91-7.82 (m, 4H, 4×—ArH), 7.31-7.23 (m, 6H, 6×—ArH), 6.93 (d, 1H, J=9.3 Hz, —ArH), 4.66-4.62 (m, 1H, —CH—), 3.79-3.77 (m, 2H, —CH$_2$—), 3.59 (q, 2H, J=10.8 Hz, —CH$_2$—), 3.04-2.85 (m, 4H, 2×—CH$_2$—), 2.27 (s, 3H, —CH$_3$), 2.01-1.90 (m, 2H, —CH$_2$—), 1.39-1.37 (m, 6H, 2×—CH$_3$); $^{13}$C NMR (75 MHz, CDCl$_3$) δ: 164.5, 163.9, 158.9, 139.7, 139.5, 135.0, 129.3, 129.2, 128.4, 128.2, 127.8, 127.2, 126.0, 124.3, 121.7, 115.3, 112.1, 70.1, 64.5, 55.6, 45.6, 37.2, 28.2, 25.7, 22.0, 16.3.

Example 22

2-(7-amino-5,6,7,8-tetrahydro-7-naphthalenemethanol)-5-(3-methyl-4-isopropoxy)-1,3,4-oxdiazole (Compound 067 in Prior Patent Application of 201110155280.X)

Compound 22 0.2 g (0.0 mmol), methanol 20 mL, ammonium formate 0.21 g (0.0 mmol), and Pd/C (10%) 0.12 g (0.0 mmol) were added to three necked bottle (100 ml), and heated to reflux and reacted under monitoring by TLC. After the completion of the reaction, the system was cooled and filtered. The filtrate was concentrated and then purified by silica gel column chromatography (developing solvent: methanol:dichloromethane=1:5) to obtain compound 067 as a white solid (0.07 g, 44% yield), mp 189-191° C.; $^1$H NMR (300 MHz, CDCl$_3$) δ: 7.93-7.85 (m, 4H, 4×—ArH), 7.39 (d, 1H, J=8.1 Hz, —ArH), 7.17 (d, 1H, J=8.4 Hz, —ArH), 4.75-4.71 (m, 1H, —CH—), 3.61 (s, 2H, —NH$_2$), 3.51-3.50 (m, 2H, —CH$_2$—), 3.09 (s, 2H, —CH$_2$—), 2.94-2.92 (m, 2H, —CH$_2$—), 2.22 (s, 3H, —CH$_3$), 2.05-2.00 (m, 2H, —CH$_2$—), 1.34-1.32 (m, 6H, 2×—CH$_3$); $^{13}$C NMR (75 MHz, CDCl$_3$) δ: 164.0, 163.6, 159.5, 134.2, 129.8, 129.0, 127.9, 127.3, 126.3, 125.7, 124.4, 121.3, 114.9, 113.1, 70.2, 63.1, 55.5, 34.2, 27.3, 25.1, 22.0, 16.1; ESI-MS: (C$_{23}$H$_{27}$N$_3$O$_3$) (M$^+$+1): 394.5, 377.7, 352.9; IR (KBr) v cm$^{-1}$: 3400, 2976, 2925, 2557, 2019, 1611, 1554, 1485, 1402, 1385, 1373, 1333, 1311, 1273, 1255, 1174, 1136, 1110, 1060, 996, 953, 874, 825, 742.

Example 23

7-[5-(3-methyl-4-isopropoxyphenyl)-2-1,3,4-oxdiazolyl]-2-ethylamino-1,2,3,4-tetrahydro-naphthalen-2-yl-methanol

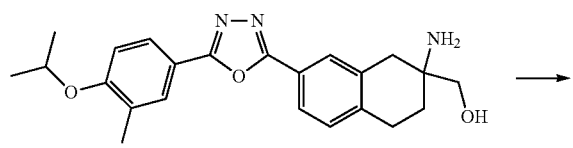

Example 22

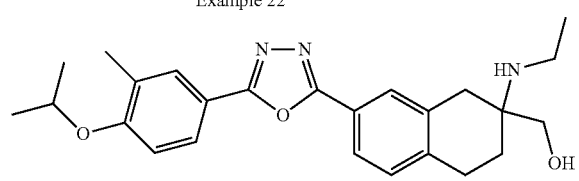

Example 23

Acetic acid (18 mg, 0.3 mmol, 1.5 eq) and acetaldehyde (40%, 35 mg, 0.3 mmol, 1.5 eq) were added to a solution of the compound obtained in Example 22 (80 mg, 0.2 mmol, 1.0 eq) in dichloromethane (30 ml). As the solvent was cooled to 0° C., sodium borohydride and NaBH(OAc)$_3$ (65 mg, 0.3 mmol, 1.5 eq) were added to the reaction mixture. The reaction solution was stirred for 5 hours, then water (50 ml) was added. The reaction mixture was adjusted to the pH of 8~9 with sodium bicarbonate, then was extracted with dichloromethane (50 ml) for three times. Organic layer was washed with salt water (30 ml), dried over anhydrous sodium sulfate, and concentrated, and solvent was eliminated under vacuum. The resulting crude product was purified by silica gel column chromatography (dichloromethane:methanol=20:1) to obtain the compound in Example 23 (20 mg, 58% yield). NMR (400 MHz, CD$_3$OD) δ=7.82 (4H, m), 7.28 (1H, m), 7.06 (1H, d), 4.70 (1H, m), 3.60 (2H, m), 3.18 (4H, m), 2.90 (2H, m), 2.20 (3H, s), 2.12 (2H, m), 1.40 (9H, m); Rt=3.79 min, MS (M+H$^+$): 422, the theoretical calculating value: 422.

Example 24

7-[5-(3-methyl-4-isopropoxyphenyl)-2-1,3,4-oxdiazolyl]-2-dimethylamino-1,2,3,4-tetrahydro-naphthalen-2-yl-methanol

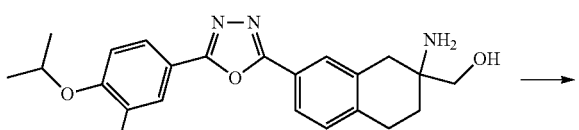

Example 22

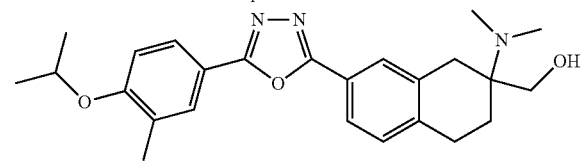

Example 24

The compound in Example 22 (30 mg) was dissolved in dichloromethane (5 ml). Formaldehyde (5 mg), glacial acetic acid (5 mg) were added, and with temperature controlled at 0° C., sodium borohydride acetate was added, and then reacted at 0° C. for 30 minutes. Dimethyl product was generated mostly in the reaction under LCMS monitoring, then purified by column chromatography to obtain the compound in Example 24 (purity: 97% by LCMS). The purity was good under the detection of HNMR (>95%). NMR (400 MHz, CD$_3$Cl$_3$) δ=7.80 (3H, m), 7.78 (1H, m), 7.15 (1H, m), 6.84 (1H, m), 4.60 (1H, m), 3.74 (2H, m), 3.15 (2H, m), 2.76 (6H, s), 2.20 (3H, s), 2.00 (2H, m), 1.42 (2H, m), 1.38 (6H, d), Rt=4.04 min, MS (M+H$^+$): 422, the theoretical calculating value: 422.

Example 25

N-{2-hydroxymethyl-7-[5-(3-methyl-4-isopropoxyphenyl)-2-1,3,4-oxdiazolyl]-1,2,3,4-tetrahydro-naphthalen-2-yl}acetamide

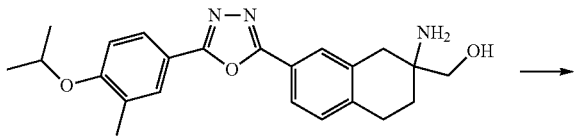

Example 22

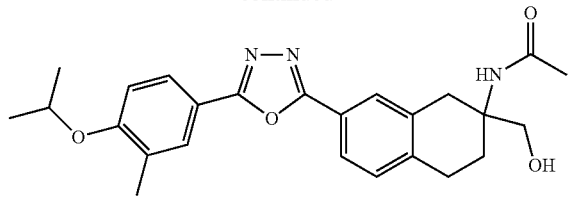

Example 25

The compound in Example 22 (100 mg, 0.25 mmol, 1.0 eq) was added to dichloromethane (10 ml), and with temperature controlled at 0° C., acetic anhydride (26 mg, 0.25 mmol, 1.0 eq) was added, then the system was reacted at room temperature for 2 hours under the monitoring of thin-layer chromatography (dichloromethane:methanol=5.1). After the completion of the reaction, water (20 ml) was added to the system, and the reaction mixture was adjusted to the pH of 8~9 with saturated $NaHCO_3$, then was extracted with dichloromethane (20 ml). Organic layer was combined, dried over anhydrous sodium sulfate, and filtered. The mother liquor was concentrated under reduced pressure, and the resulting crude product was purified by column chromatography (dichloromethane:methane=30:1) to obtain the compound in Example 25 (50 mg, 46%) as a white solid. NMR (400 MHz, DMSO-$d_6$) δ=7.93 (2H, d), 7.83 (2H, d), 7.38 (1H, s), 7.30 (1H, d), 7.15 (1H, d), 4.72 (1H, m), 3.64 (3H, m), 3.22 (2H, m), 2.99 (1H, d), 2.86 (2H, m), 2.23 (3H, s), 1.75 (3H, s), 1.34 (3H, s), 1.32 (3H, s); Rt=3.66 min, MS (M+H$^+$): 436, the theoretical calculating value: 436.

Example 26

N-{2-hydroxymethyl-7-[5-(3-methyl-4-isopropoxyphenyl)-2-1,3,4-oxdiazolyl]-1,2,3,4-tetrahydronaphthalen-2-yl}methanesulfonamide

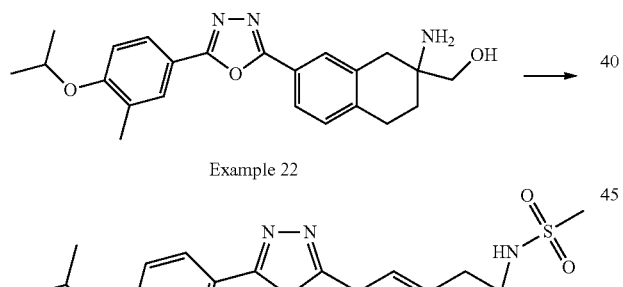

The compound in Example 22 (100 mg, 0.25 mmol, 1.0 eq) was added to tetrahydrofuran (10 ml) and water (10 ml). $K_2CO_3$ (172 mg, 1.25 mmol, 5.0 eq) was added and then stirred for 30 minutes. After that, as the reaction mixture was cooled to 0° C., methanesulfonyl chloride (45 mg, 0.38 mmol, 1.5 eq) was added, then the system was reacted at room temperature for 2 hours, with monitoring by thin-layer chromatography (dichloromethane:methanol=5:1) and LCMS. After the completion of the reaction, water (20 ml) was added, and reaction mixture was extracted with dichloromethane (20 ml) for three times. Organic layer was dried and concentrated, then the resulting crude product was purified by column chromatography (dichloromethane:methanol=100:1) to obtain the compound in Example 26 (30 mg, 25%) as a yellow solid.

NMR (400 MHz, CDCl$_3$) δ=7.93 (3H, m), 7.85 (1H, s), 7.28 (1H, d), 6.94 (1H, d), 4.62 (1H, m), 3.84 (2H, m), 3.02 (2H, m), 2.94 (2H, m), 2.31 (3H, s), 1.85 (2H, m), 1.47 (3H, s), 1.40 (3H, s), 1.24 (3H, s); Rt=3.69 min, MS (M+H$^+$): 472, the theoretical calculating value: 472.

Reaction Scheme 7: Synthesis of the Compound in Example 27

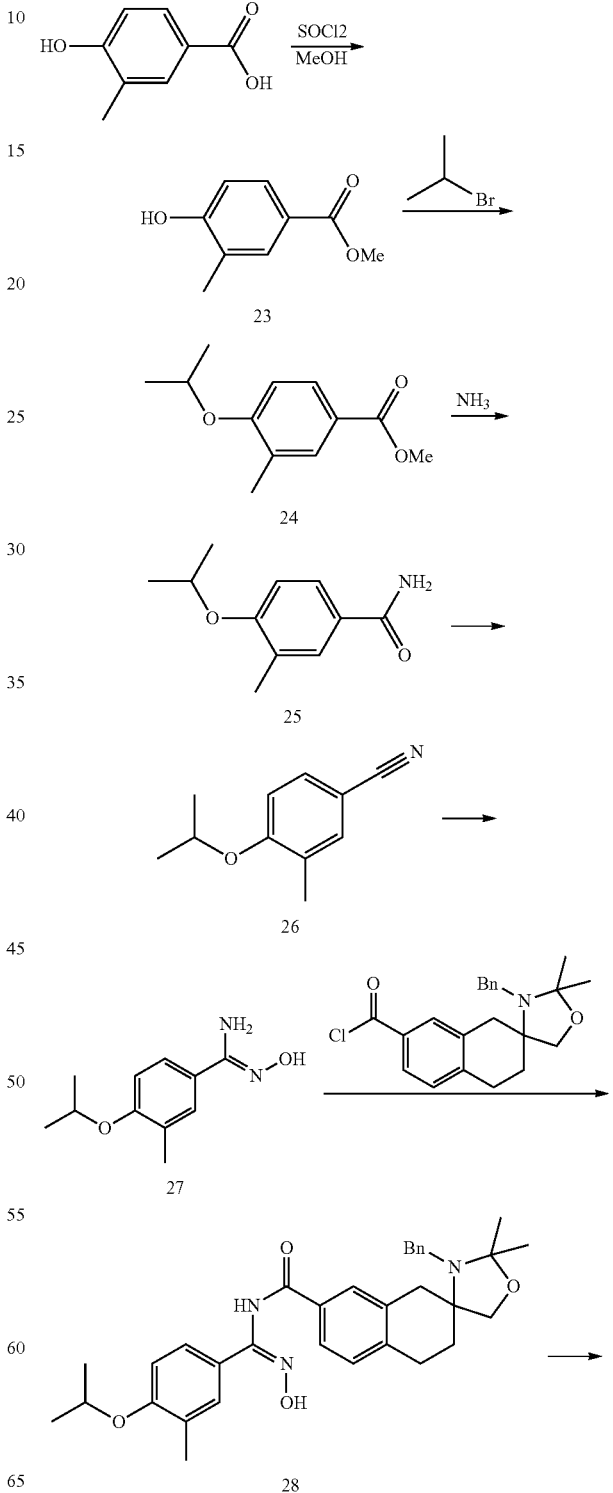

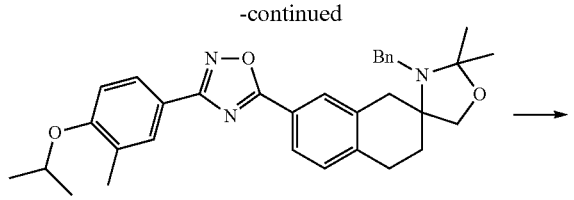

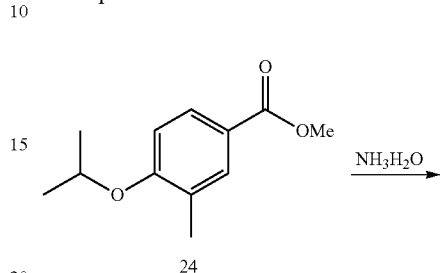

Example 27

Preparation of Intermediate 23:

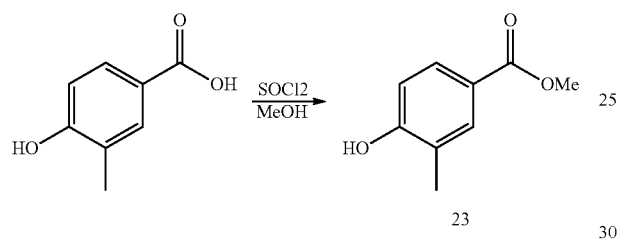

Raw material 4-hydroxy-3-methyl benzoic acid (100 g, 0.66 mol, 1.0 eq) was dissolved in methanol (500 ml). As the system was cooled to 0° C. in ice-salt bath, SOCl$_2$ (200 ml) was added dropwise. Then the system was heated to reflux, and reacted for 5 hours under monitoring by thin-layer chromatography (ethyl acetate:petroleum ether=1:3). After the completion of the reaction, the mixture was concentrated under reduced pressure. The resulting residue was dissolved in ethyl acetate, and washed once with saturated NaHCO$_3$, then washed once with water. The organic layer was dried over anhydrous sodium sulfate, and filtered. The mother liquor was concentrated to obtain the intermediate compound 23 (10 g, 92%) as yellow oil.

Preparation of the Intermediate 24:

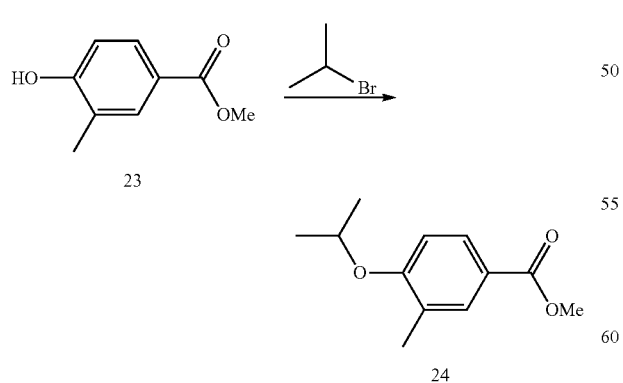

Intermediate 23 (10 g, 52 mmol, 1.0 eq) was dissolved in DMF (100 ml). K$_2$CO$_3$ (21 g, 0.015 mol, 3.0 eq) and 2-bromo isopropane (13.0 g, 0.1 mol, 2.0 eq) were added. The system was heated to 130° C. and reacted for 15 hours, under monitoring by thin-layer chromatography (ethyl acetate:petroleum ether=1:5). After the completion of the reaction, the system was left to cool to the room temperature. Water (100 ml) was added to the system, which was then extracted with ethyl acetate (100 ml). The organic layer was combined, washed once with saturated aqueous sodium chloride, dried over anhydrous sodium sulfate, filtered, and concentrated to obtain intermediate compound 24 (12 g, 92%) as yellow oil.

Preparation of the Intermediate 25:

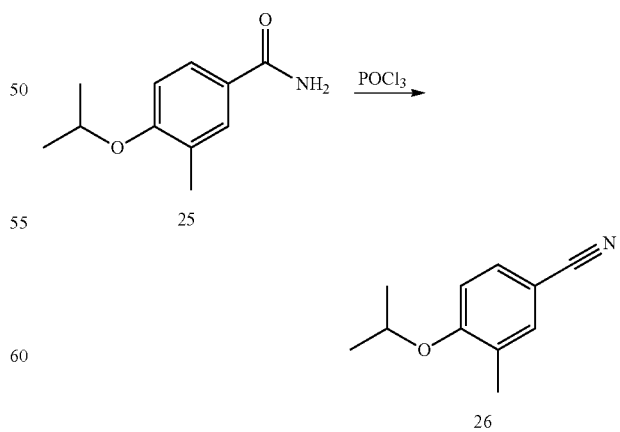

Raw material 24 (5 g, 24 mmol, 1.0 eq) was dissolved in ethanol (50 ml), wherein NH$_3$H$_2$O (20 ml) was added. The reaction system was heated to 120° C. for 15 hours. The reaction progress was monitored by thin-layer chromatography (ethyl acetate:petroleum ether=1:5). After completion of the reaction, the system was concentrated under reduced pressure. Water (100 ml) was added to the residue, which was extracted with ethyl acetate (100 ml) for three times. The organic layer was combined, dried over anhydrous sodium sulfate, and filtered. The mother liquor was concentrated under reduced pressure, and the resulting residue was purified by column chromatography (ethyl acetate:petroleum ether=5:1) to obtain intermediate compound 25 (3.0 g, 67%) as a white solid.

Preparation of the Intermediate 26:

Raw material 25 (100 mg, 0.52 mmol, 1.0 eq) was dissolved in POCl$_3$ (5 ml). The system was heated to reflux and reacted for 5 hours, under monitoring by thin-layer chromatography (ethyl acetate:petroleum ether=1:5). After completion of reaction, the system was concentrated under reduced pressure. The resulting residue was added to ice water (20 ml), and then extracted with ethyl acetate (100 ml) for three times. The organic layer was combined, dried over anhydrous sodium sulfate, and filtered. The mother liquor was concentrated under reduced pressure, then purified by column chromatography (ethyl acetate:petroleum ether=1:10) to obtain intermediate compound 26 (60 mg, 67%) as yellow oil.

Preparation of the Intermediate 27:

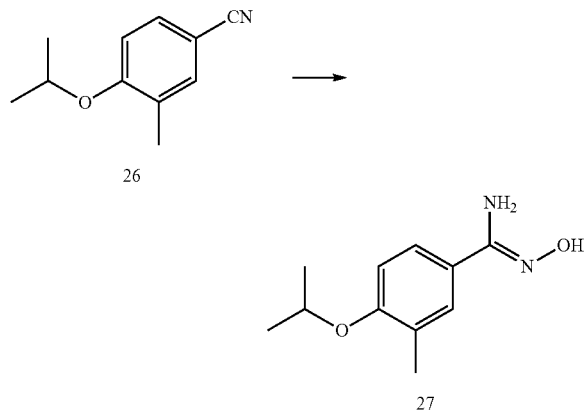

Raw material 26 (500 mg, 2.9 mmol, 1.0 eq) was dissolved in methanol (10 ml). Hydroxylamine hydrochloride (520 mg, 5.8 mmol, 2.0 eq) and $K_2CO_3$ (800 mg, 5.8 mmol, 2.0 eq) were added to the system. Then, the system was heated to reflux and reacted overnight, and the reaction was monitored by thin-layer chromatography (ethyl acetate:petroleum ether=1:5). After completion of the reaction, the reaction system was cooled to the room temperature and concentrated under reduced pressure. Water (30 ml) was added, and the mixture was extracted with dichloromethane (30 ml) for three times. The organic layer was combined, washed once with aqueous sodium chloride, dried over anhydrous sodium sulfate, filtered, and concentrated under reduced pressure to give a crude product, which was purified by column chromatography (ethyl acetate:petroleum, ether=1:5) to obtain intermediate compound 27 (300 mg, 50%) as a yellow solid.

Preparation of the Intermediate 28:

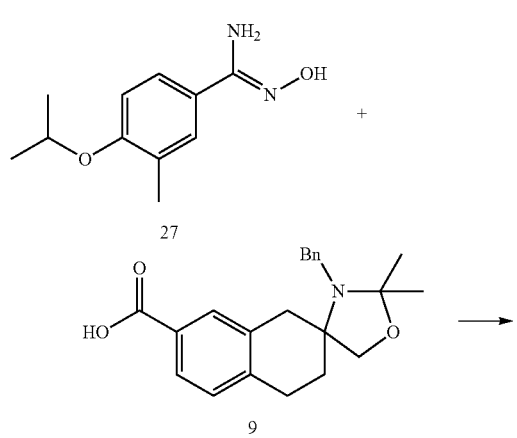

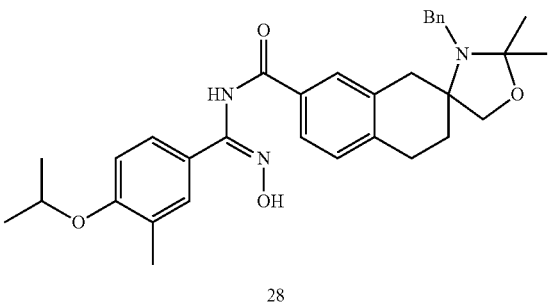

Raw material 27 (150 mg, 0.7 mmol, 1.0 eq) and raw material 9 (250 mg, 0.7 mmol, 1.0 eq) were dissolved in dichloromethane (10 ml). DIC (130 mg, 1.1 eq, 1.5 eq) was added to the mixture. After that, the system was reacted at room temperature overnight, and the reaction was monitored by thin-layer chromatography (ethyl acetate:petroleum ether=1:5) and LCMS. After the completion of reaction, water (20 ml) was added to the system, which was then extracted with dichloromethane (30 ml) for three times. The organic layer was combined, washed once with aqueous sodium, chloride solution, dried over anhydrous sodium sulfate, and filtered, then concentrated under reduced pressure and purified by column chromatography (ethyl acetate:petroleum ether=1:5) to obtain intermediate compound 28 (80 mg, 21%) as a while solid.

Preparation of the Intermediate 29:

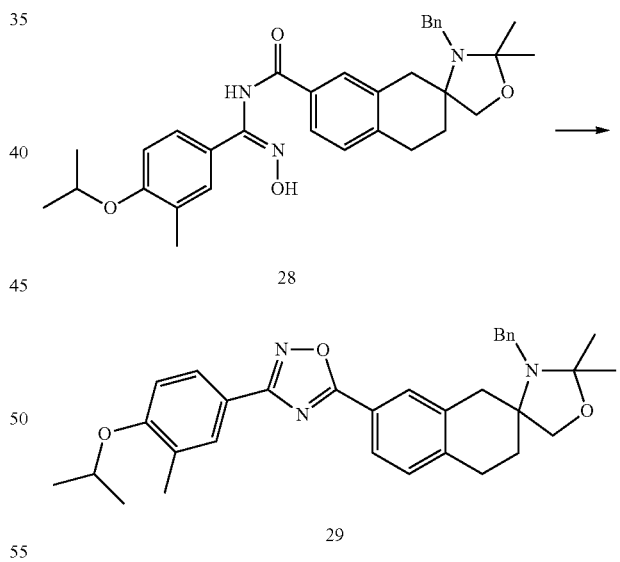

Raw material 28 (30 mg, 0.05 mmol, 1.0 eq) was added to tetrahydrofuran (10 ml). Tetrabutylammonium fluoride (30 mg) was added to the system. Then, the system was reacted at room temperature overnight, under monitoring of thin-layer chromatography (ethyl acetate:petroleum ether=1:5) and LCMS. After completion of reaction, water (20 ml) was added to the system, which was then extracted with ethyl acetate (20 ml) for three times. The organic layer was combined, washed with saturated aqueous sodium chloride (20 ml), dried over anhydrous sodium sulfate, and filtered. The mother liquor was concentrated under reduced pressure to give a crude product, which was purified by column chromatography (ethyl acetate:petroleum ether=1:10) to obtain intermediate compound 29 (15 mg, 52%) as a white solid.

Example 27

7-[3-(3-methyl-4-isopropoxyphenyl)-5-1,2,4-oxdiazolyl]-2-amino-1,2,3,4-tetrahydro-naphthalen-2-yl-methanol

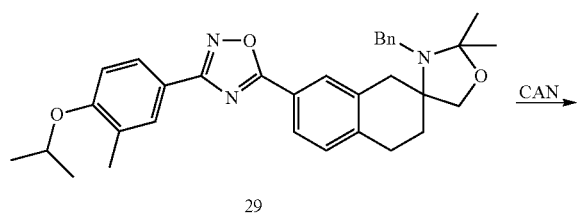

29

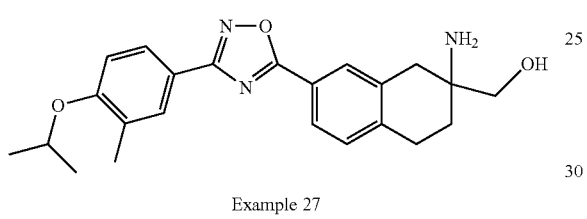

Example 27

Raw material 29 (45 mg, 0.09 mmol, 1.0 eq) and ceric ammonium nitrate (45 mg) were added to acetonitrile (10 ml) and dichloromethane (1 ml). The system was reacted at room temperature for 5 hours under the monitoring of thin-layer chromatography (dichloromethane:methanol=10:1) and LCMS. After the completion of reaction, water (20 ml) was added to the system, which was then extracted with dichloromethane (20 ml) for three times. The organic layer was combined, washed with saturated aqueous sodium chloride (20 ml), dried over anhydrous sodium sulfate, and filtered. The mother liquor was concentrated under reduced pressure to give a crude product, which was purified by column chromatography (dichloromethane:methanol=50:2) to obtain the compound its Example 27 (20 mg, 61%) as a white solid.

NMR (400 MHz, DMSO-$d_6$) δ=7.93 (1H, m), 7.87 (2H, s), 7.71 (1H, dd), 7.42 (1H, d), 7.14 (1H, s), 4.75 (1H, m), 3.42 (2H, s), 2.92 (4H, m), 2.22 (3H, s), 1.88 (2H, m), 1.32 (6H, m); Rt=4.10 min, MS (M+H$^+$): 394, the theoretical calculating value: 394.

Example 28

6-[3-(3-methyl-4-isopropoxyphenyl)-5-1,2,4-oxdiazolyl]-2-amino-1,2,3,4-tetrahydro-naphthalen-2-yl-methanol, which was Prepared According to the Synthesis Methods Similarly as Those of Example 27

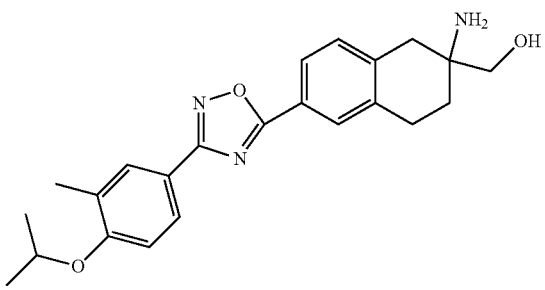 [SMILES: Cc1cc(-c2noc(-c3ccc4c(c3)CCC(N)(CO)C4)n2)ccc1OC(C)C]

NMR (400 MHz, DMSO-$d_6$) δ=7.9 (4H, m), 7.21 (1H, m), 7.41 (2H, m), 6.9 (1H, m), 6.80 (1H, m), 4.62 (1H, m), 3.70 (2H, m), 3.50 (2H, m), 2.80 (2H, m), 2.32 (3H, s), 1.42 (2H, m), 1.38 (6H, d), Rt=4.10 min, MS (M+H$^+$): 394, the theoretical calculating value: 394.

Reaction Scheme 8: Synthesis of Example 29

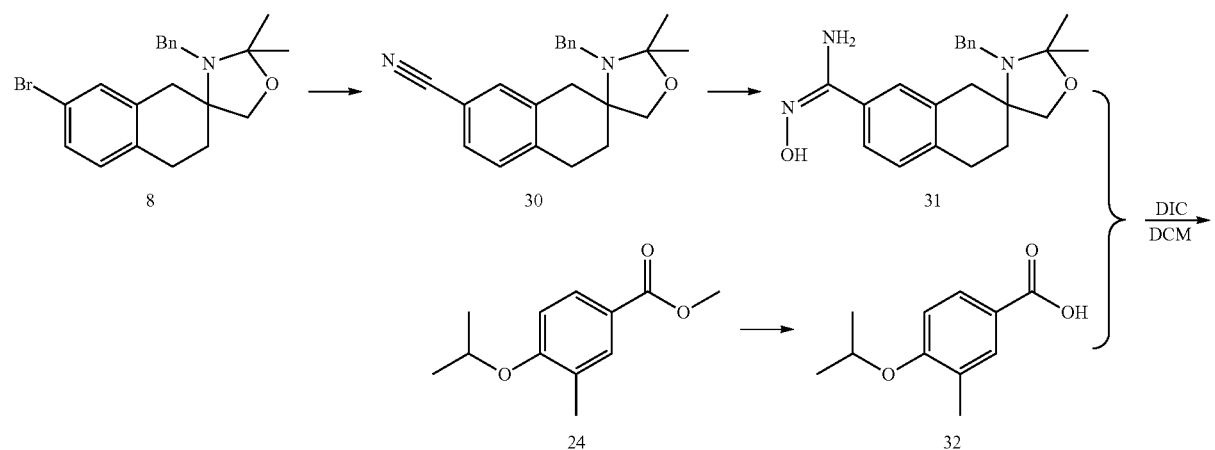

-continued

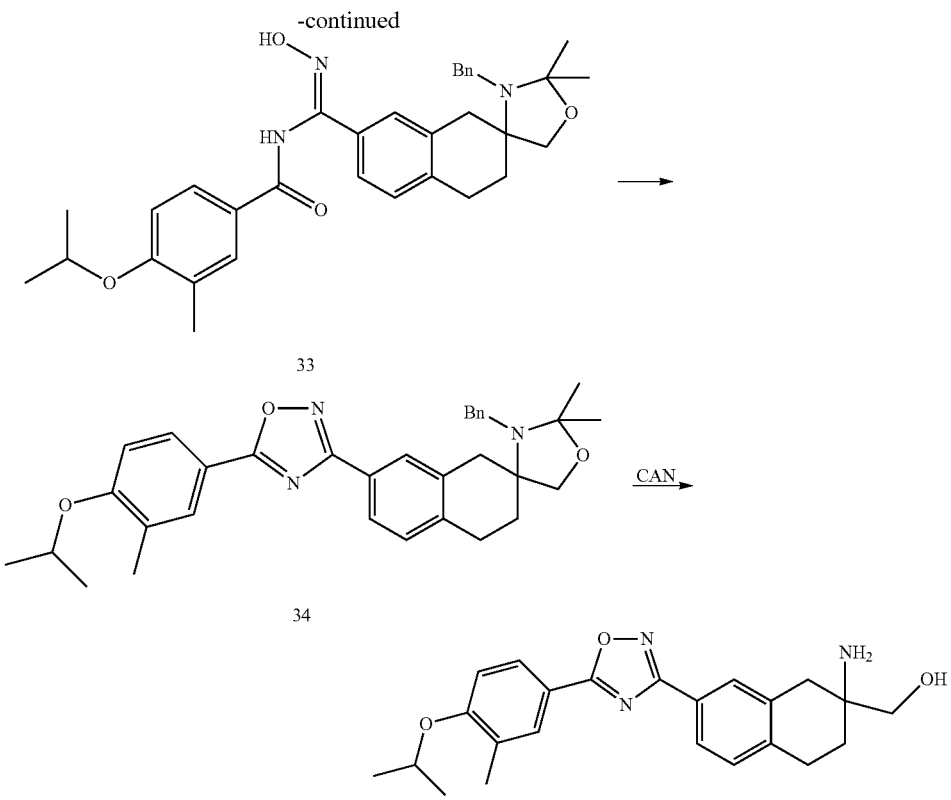

Example 29

Preparation of the Intermediate 30

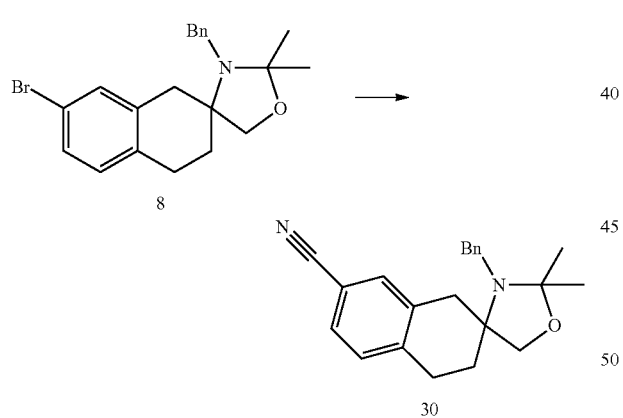

Preparation of the Intermediate 31:

Raw material 8 (1.0 g, 2.6 mmol, 1.0 eq), K₄Fe(CN)₆·3H₂O (2.2 g, 5.2 mmol, 2.0 eq) and PtOAc (10 mg, cat.) were added to DMAC (20 ml), and the system was heated to 120° C. and reacted overnight. After completion of the reaction, water (20 ml) was added to the system, which was then extracted with ethyl acetate (20 ml) for three times. The organic layer was combined, washed once with saturated aqueous sodium chloride solution, dried over anhydrous sodium sulfate, and filtered. The mother liquor was concentrated under reduced pressure to give a crude product, which was purified by column chromatography (ethyl acetate:petroleum ether=1:10) to obtain intermediate compound 30 (0.3 g, 35%) as a white solid.

Raw material 30 (300 mg, 0.9 mmol, 1.0 eq), hydroxylamine hydrochloride (110 mg, 1.8 mmol, 2.0 eq) and K₂CO₃ (370 mg, 2.7 mmol, 3.0 eq) were added to methanol (10 ml), and the system was heated by microwave to 80° C. and reacted for 5 hours. After completion of the reaction, water (20 ml) was added to the system, which was then extracted with dichloromethane (20 ml) for three times. The organic layer was combined, washed once with saturated aqueous sodium chloride solution, dried over anhydrous sodium sulfate, and filtered. The mother liquor was concentrated under reduced pressure to give a crude product, which was purified by column chromatography (methanol:dichloromethane=1:30) to obtain intermediate compound 31 (150 mg, 46%) as a white solid.

Preparation of the Intermediate 32:

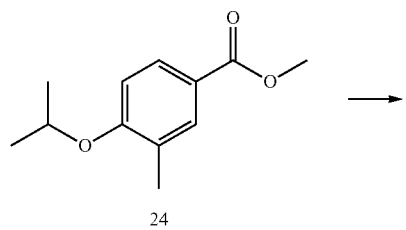

Raw material 24 (5.0 g, 24 mmol, 1.0 eq) and sodium hydroxide (2.9 g, 72 mmol, 3.0 eq) were added to the mixture of methanol (30 ml) and water (20 ml), and reacted at room temperature overnight. After completion of the reaction, water (50 ml) was added to the system. The reaction solution was adjusted to pH of 4 with diluted hydrochloric acid and then filtered. The filter cake was collected and dried to obtain intermediate compound 32 (3.5 g, 76%) as a white solid.

Preparation of the Intermediate 33:

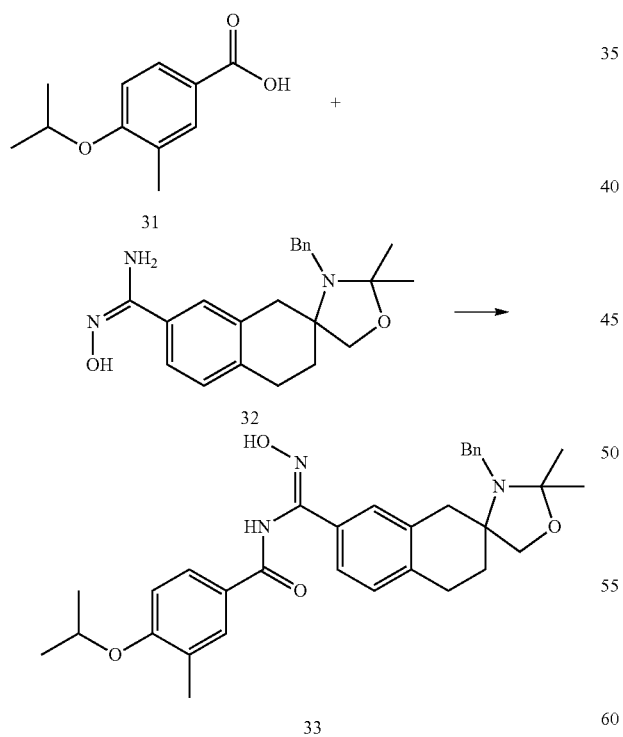

Raw material 31 (100 mg, 0.27 mmol, 1.0 eq) and 32 (60 mg, 0.3 mmol, 1.1 eq) were added to dichloromethane (10 ml), and DIC (50 mg, 0.4 mmol, 1.5 eq) was added to the system at room temperature. After that, the system was reacted at room temperature for 5 hours. As the reaction completed, water (20 ml) was added to the system, which was then extracted with dichloromethane (20 ml) for three times. The organic layer was combined, dried over anhydrous sodium sulfate, and filtered. The mother liquor was concentrated under reduced pressure to give a crude product, which was purified by column chromatography (dichloromethane:methanol=50:1) to obtain intermediate compound 33 (60 mg, 41%) as a white solid.

Preparation of the Intermediate 34:

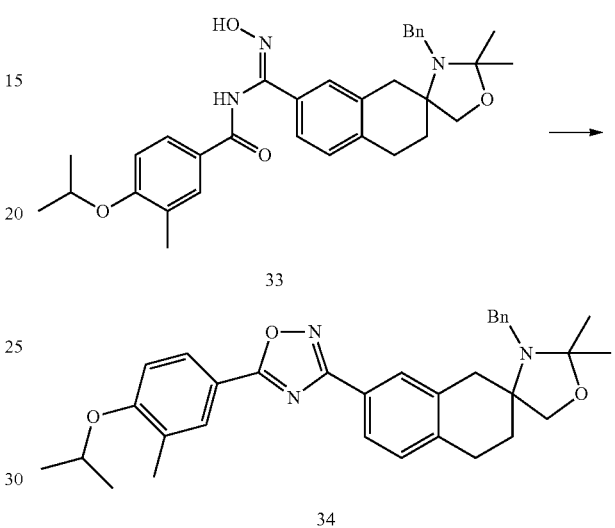

Raw material 33 (100 mg, 0.18 mmol, 1.0 eq) and TBAF (tetrabutylammonium fluoride) (96 mg, 0.36 mmol, 2.0 eq) were added to tetrahydrofuran (10 ml), and reacted at room temperature for 6 hours. The reaction was monitored by thin-layer chromatography (ethyl acetate:petroleum ether=1:2). After completion of the reaction, water (20 ml) was added to the system, which was then extracted with dichloromethane (20 ml) for three times. The organic layer was combined, dried over anhydrous sodium sulfate, and filtered. The mother liquor was concentrated under reduced pressure to give a crude product, which was purified by column chromatography (dichloromethane:methanol=30:1) to obtain intermediate compound 34 (60 mg, 62%) as a white solid.

Example 29

7-[5-(3-methyl-4-isopropoxyphenyl)-3-1,2,4-oxdiazolyl]-2-amino-1,2,3,4-tetrahydro-naphthalen-2-yl-methanol

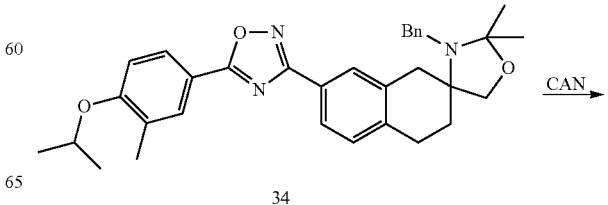

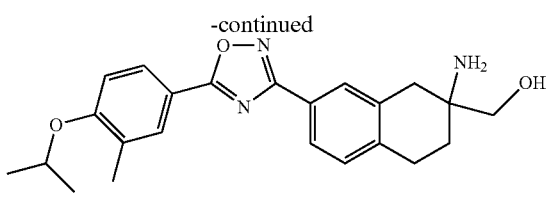

Example 29

Raw material 34 (60 mg, 0.11 mmol, 1.0 eq) and CAN (ceric ammonium nitrate) (60 mg) were added to the mixture of acetonitrile (10 ml) and dichloromethane (2 ml), then reacted at room temperature for 6 hours. The reaction was monitored by thin-layer chromatography (dichloromethane: methanol=5:1). After completion of the reaction, water (20 ml) was added to the system. The reaction solution was adjusted to pH of 8 with saturated $NaHCO_3$ solution, and then was extracted with dichloromethane (20 ml) for three times. The organic layer was combined, washed once with saturated aqueous sodium chloride, dried over anhydrous sodium sulfate and filtered. The mother liquor was concentrated under reduced pressure to give a crude product, which was purified by column chromatography (dichloromethane:methanol=10:1) to obtain Example 29 (30 mg, 66%) as a white solid.

NMR (400 MHz, $CDCl_3$) δ=7.91 (2H, d), 7.82 (2M, m), 7.47 (1H, s), 7.14 (1H, d), 6.85 (1H, d), 4.61 (1H, m), 3.71 (2H, s), 3.06 (2H, m), 2.88 (2H, m), 2.24 (3H, s), 2.04 (2H, m), 1.27 (6H, m); Rt=4.38 min, MS (M+H$^+$): 394, the theoretical calculating value: 394.

Example 30

6-[5-(3-methyl-4-isopropoxyphenyl)-3-1,2,4-oxdiaz-olyl]-2-amino-1,2,3,4-tetrahydro-naphthalen-2-yl-methanol, Which Was Prepared According to the Synthesis Methods Similarly as Those of Example 29

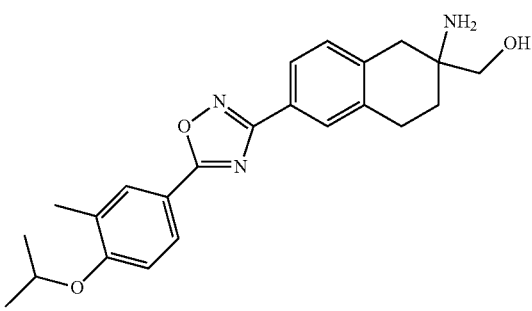 [SMILES: Cc1cc(-c2nc(-c3ccc4c(c3)CCC(N)(CO)C4)no2)ccc1OC(C)C]

NMR (400 MHz, DMSO-$d_6$) δ=8.00 (2H, m), 7.8 (2H, m), 7.2 (2H, m), 4.82 (1H, m), 3.40 (2H, m), 3.20 (2H, m), 2.80 (2H, m), 2.22 (3H, s), 1.42 (2H, m), 1.38 (6H, d), Rt=4.32 min, MS (M+H$^+$): 394, the theoretical calculating value: 394.

Reaction Scheme 8: Synthesis of Example 31

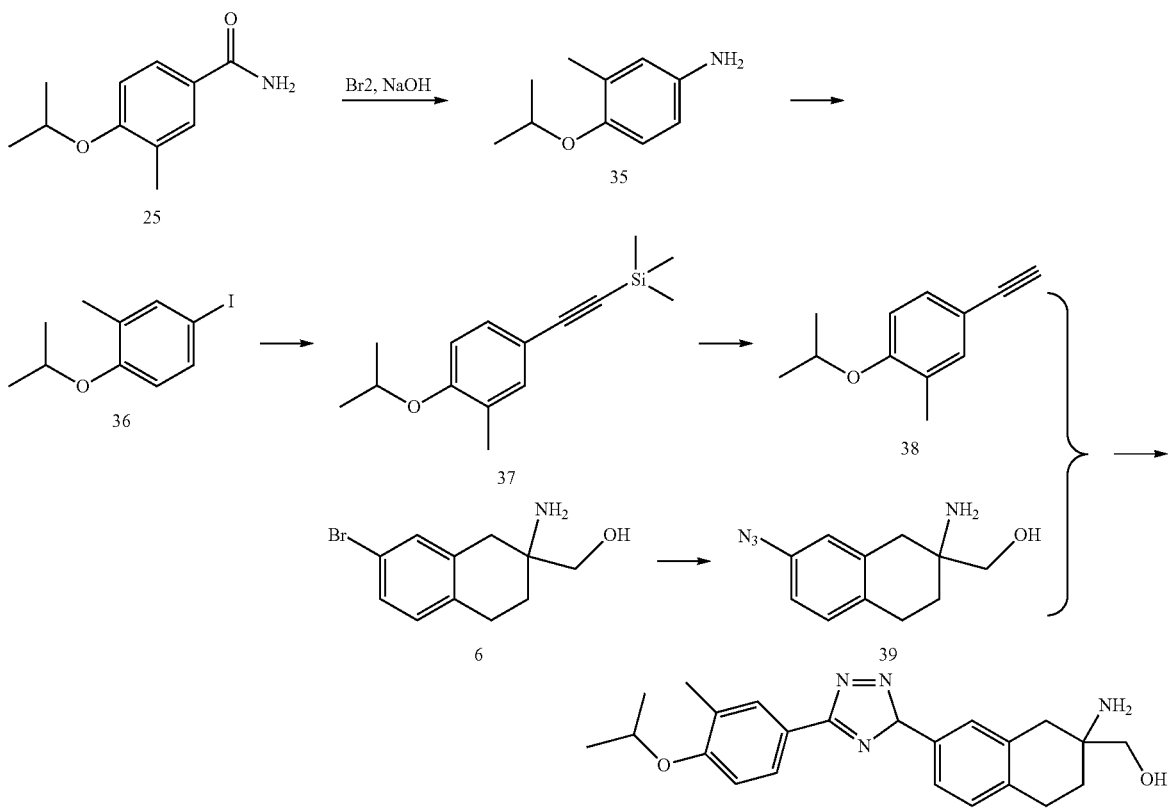

Example 31

Preparation of the Intermediate 35:

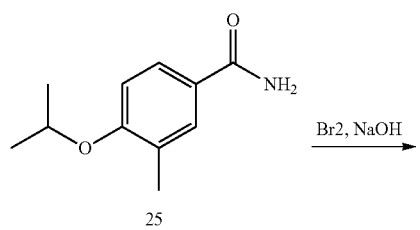

Raw material 25 (4.8 g, 25 mmol) and bromine (5.0 g, 31 mmol, 1.2 eq) were added to a solution of sodium hydroxide (4 g, 100 mmol, 3.8 eq) at 0° C. The reaction system was then heated to 75° C. After 12 hours of reaction, the system was cooled to the room temperature, and extracted with ethyl acetate (3×100 ml) for three times. The organic layer was combined, washed once with saturated aqueous sodium chloride solution, dried over anhydrous sodium sulfate and filtered. The mother liquor was concentrated under reduced pressure to give a crude product, which was purified by column chromatography (ethyl acetate:petroleum ether=10:1) to obtain intermediate compound 35 (1 g, 66% yield) as brown oil.

Preparation of the Intermediate 36:

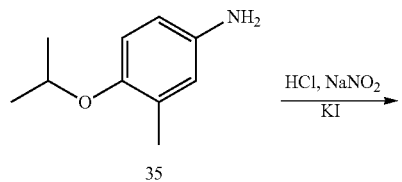

Raw material 35 (2.5 g, 15 mmol, 1.0 eq) was added to hydrochloric acid (50 ml) at 0° C. The resulting solution was added to the aqueous solution (10 ml) of sodium nitrite (1.2 g, 17 mmol, 1.2 eq) at 0° C. The reaction solution was stirred at room temperature for 4 hours, and the resulting mixture was extracted with ethyl acetate (50 ml) for three times. The organic layer was combined, washed once with saturated aqueous sodium chloride solution, dried over anhydrous sodium sulfate and filtered. The mother liquor was concentrated under reduced pressure to give a crude product, which was purified by column chromatography (ethyl acetate:petroleum ether=30:1) to obtain intermediate compound 36 (2.1 g, 50% yield) as yellow oil.

Preparation of the Intermediate 38:

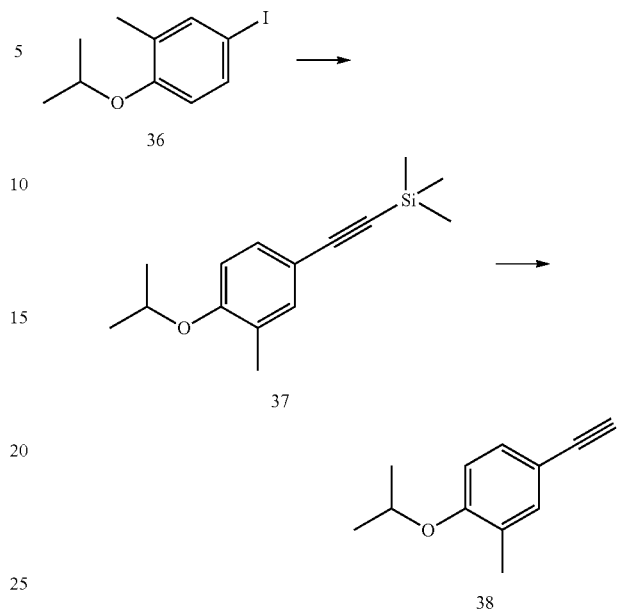

Under nitrogen atmosphere, cupric iodide (50 mg, cat.), Pd(PPh$_3$)$_4$ (50 mg, cat.), triethylamine (3.2 g, 32 mmol, 9.0 eq) and ethynyltrimethylsilane (1.0 g, 11 mmol, 3.0 eq) were added to the solution of raw material 36 (1.0 g, 3.6 mmol, 1.0 eq) in methylbenzene (10 ml) under N$_2$ atmosphere. The reaction solution was stirred at 85° C. for 12 hours, under monitoring of MS and thin-layer chromatography (ethyl acetate:petroleum ether=1:10). As the system was cooled to room temperature, TBAF (100 mg) was added. The reaction mixture was stirred at room temperature for 2 hours and then was extracted with ethyl acetate (50 ml) for three times. The organic layer was combined, washed with saturated aqueous sodium chloride, dried over anhydrous sodium sulfate and filtered. The mother liquor was concentrated under reduced pressure to give a crude product, which was purified by column chromatography (ethyl acetate:petroleum ether=1:10) to obtain intermediate compound 37 (0.5 g, 79%) as yellow oil.

Preparation of the Intermediate 39:

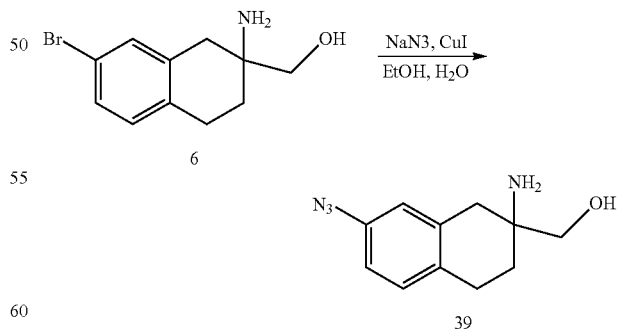

The intermediate 6 (1.0 g, 4 mmol, 1.0 eq), sodium azide (0.8 g, 12 mmol, 3.0 eq), cupric iodide (40 mg, 0.05 eq) and N1,N2-dimethyl ethylene-1,2-diamine (40 mg, 0.1 eq) were mixed with ethanol (7 ml) and water (3 ml), and the system was stirred at 100° C. for 6 hours. The reaction was monitored by MS and thin-layer chromatography (dichloromethane:methanol=10:1). After completion of the reaction, the system was extracted with dichloromethane (50 ml) for three times. The organic layer was combined, washed with saturated aqueous sodium chloride solution, dried over anhydrous sodium sulfate and filtered. The mother liquor was concentrated under reduced pressure to give a crude product, which was purified by silica gel column chromatography (ethyl acetate:petroleum ether=30:1) to obtain intermediate compound 39 (0.5 g, 59% yield) as brown oil.

Example 31

7-[4-(3-methyl-4-isopropoxyphenyl)-1-1,2,3-triaz-olyl]-2-amino-1,2,3,4-tetrahydro-naphthalen-2-yl-methanol

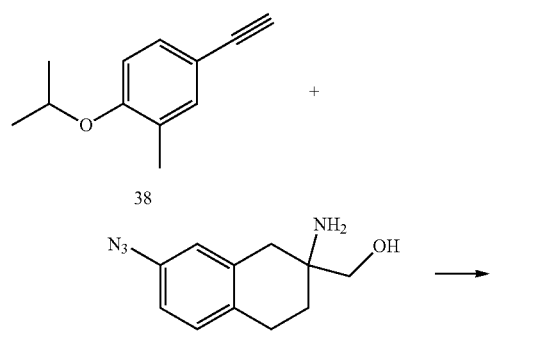

Example 31

Under nitrogen atmosphere, intermediate 38 (100 mg, 0.57 mmol, 1.0 eq), intermediate 39 (120 mg, 1.0 eq, 0.57 mmol), cupric sulfate (20 mg, CAT) and sodium ascorbate (110 mg, 0.23 mmol, 1.0 eq) were added to N,N-dimethylformamide (10 ml). The reaction mixture was stirred at room temperature for 3 hours, which was monitored by MS and thin-layer chromatography (dichloromethane:methanol=10:1). After completion of the reaction, water (20 ml) was added and then was extracted with dichloromethane (30 ml) for three times. The system was washed once with aqueous sodium chloride solution (30 ml). The organic layer was combined, washed with saturated aqueous sodium chloride, dried over anhydrous sodium sulfate and filtered. The mother liquor was concentrated under reduced pressure to give a crude product, which was purified by column chromatography (dichloromethane:methanol=20:1) to obtain Example 31 (30 mg, 14%) as a brown solid.

NMR (400 MHz, CDCl$_3$) δ=8.02 (1H, s), 7.54 (2H, m), 7.42 (1H, m), 6.92 (1H, m), 6.82 (1H, m), 4.45 (1H, m), 3.60 (2H, s), 3.04 (2H, m), 2.76 (2H, m), 2.14 (3H, s), 1.98 (2H, m), 1.24 (6H, d) Rt=3.84 min, MS (M+H$^+$): 393, the theoretical calculating value: 393.

Reaction Scheme 9: Synthesis of Example 32

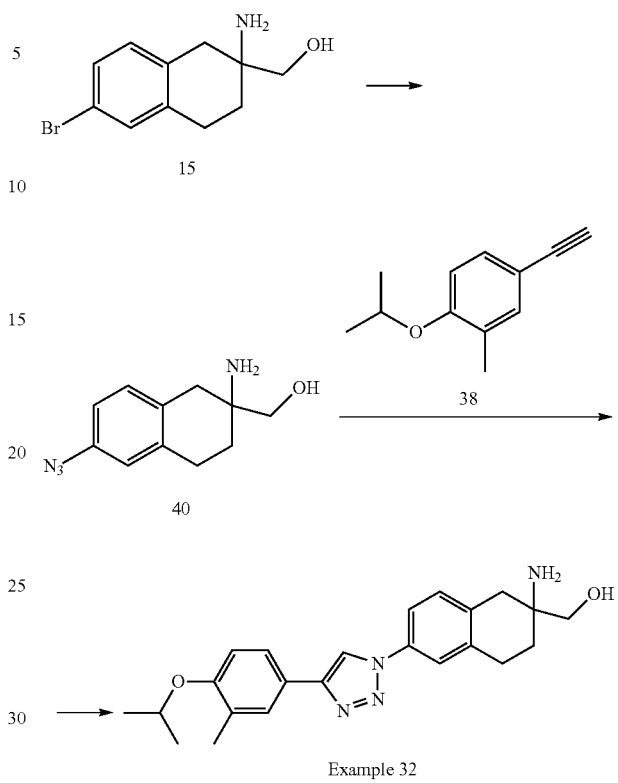

Example 32

Preparation of the Intermediate 40:

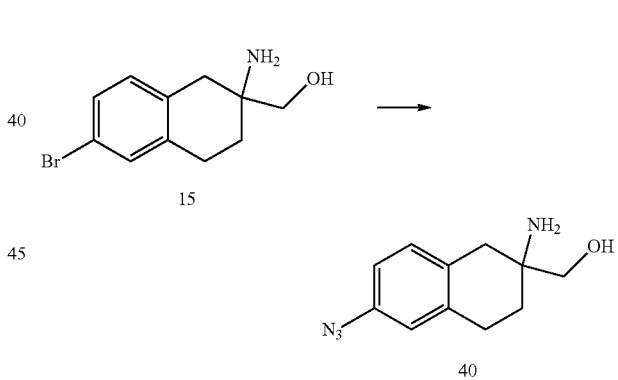

The intermediate 15 (300 mg, 1.2 mmol, 10 eq), sodium azide (240 mg, 12 mmol, 3.0 eq), cupric iodide (10 mg, 0.05 eq) and N1,N2-dimethyl ethylene-1,2-diamine (10 mg, 0.1 eq) were added to the mixture of ethanol (7 ml) and water (3 ml), and was then stirred at 100° C. for 6 hours. The reaction was monitored by MS and thin-layer chromatography (dichloromethane:methanol=10:1). After completion of the reaction, the system was extracted with dichloromethane (50 ml) for three times. The organic layer was combined, washed once with saturated aqueous sodium chloride solution, dried over anhydrous sodium sulfate and filtered. The mother liquor was concentrated under reduced pressure to give a crude product, which was purified by column chromatography (dichloromethane:methanol=30:1) to obtain intermediate compound 40 (0.2 g, 78% yield) as brown oil.

Example 32

6-[4-(3-methyl-4-isopropoxyphenyl)-1-1,2,3-triazolyl]-2-amino-1,2,3,4-tetrahydro-naphthalen-2-yl-methanol

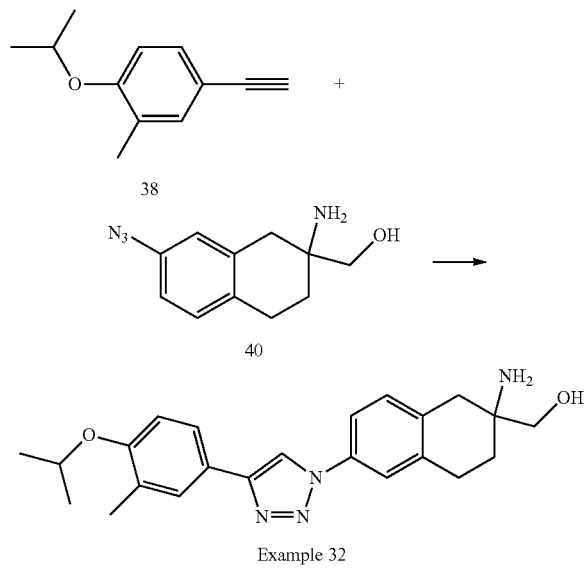

Example 32

Under nitrogen atmosphere, intermediate 38 (100 mg, 0.57 mmol, 1.0 eq), intermediate 40 (120 mg, 0.57 mmol, 1.0 eq), copper sulfate (20 mg, cat.) and sodium ascorbate (110 mg, 0.23 mmol, 1.0 eq) were added to N,N-dimethyl formamide (10 ml), and the reaction mixture was stirred at room temperature for 3 hours. The reaction was monitored by MS and thin-layer chromatography (dichloromethane:methanol=10:1). After completion of the reaction, water (20 ml) was added and was then extracted with dichloromethane (30 ml) for three times. The organic layer was combined, washed with saturated aqueous sodium chloride solution (30 ml), dried over anhydrous sodium sulfate and filtered. The mother liquor was concentrated under reduced pressure to give a crude product, which was purified by column chromatography (dichloromethane:methanol=20:1) to obtain Example 32 (40 mg, 18% yield) as a brown solid.

NMR (400 MHz, DMSO-$d_6$) δ=9.10 (1H, s), 7.74 (4H, m), 7.35 (1H, m), 7.05 (1H, m), 4.65 (1H, m), 3.10 (2H, s), 3.02 (2H, m), 2.90 (4H, m), 2.20 (3H, s), 1.30 (6H, d); Rt=3.43 min, MS (M+H$^+$): 393, the theoretical calculating value: 393.

1. $S_1P_1$GTPγS Binding Assay

Experimental Materials
1) CHO—$S_1P_1$ cell lines
2) T-75 cell culture plate; 150 mm cell culture dish
3) DMEM cell culture fluid; 10% (v/v) fetal bovine serum; 100 U/ml penicillin-100 μg/ml streptomycin; 2 mM L-oryzanol, 1 mg/ml G-418
4) Cell Lysis Buffer: HEPES 20 mM (pH 7.4), EDTA 10 mM
5) Stock solution: HEPES 20 mM, EDTA 0.1 mM
6) Binding Buffer; HEPES 20 mM (pH 7.4), NaCl 100 mM, MgCl$_2$ 5 mM, GDP 1 μM, BSA 0.1% (w/v), DMSO 2.5% (v/v),
7) Washing solution: NaH$_2$PO$_4$ 10 mM (pH 7.4)

Equipment
Super clean bench for cell culture
Cell Cradling machine
Beckman centrifugal machine
Microporous (MicroBeta) 96-well collector
2450 MicroBeta$^{2TM}$ Liquid scintillation counter/detector Test Method
The test compounds were dissolved in DMSO and prepared as a concentration of 20 mM.
The concentrations of the compounds were detected ranging from 0.3 nM to 20 μM.
Control group: 10 M SIP and SEW2871 were used as positive control and were purchased from Tocris company, and the binding buffet was as negative control.

Test method: wetting membranes by saponin solution, and preparing [$^{35}$S]-GTPγS in binding solution (4×). The test compound was prepared as 4× of the final concentration which was then performed serial 3× dilution in 100% DMSO. Membranes with high-expressed S1P1 were collected in 5 ml binding buffer, and 50 μL was added to 96-well (containing 5 μg membrane protein with high-expressed S1P1). 25 μL, test compound was added in each well. The compound was incubated with the membranes for 30 min at room temperature, then 25 μL [$^{35}$S]-GTPγS was added, and the experiment was initiated. The 96-well detection plate was incubated for 1 hour at room temperature, filtered by filtermat B, and washed with washing solution for three times. After the plate was dried for 1 h at 50° C., 8 ml scintillator solution was added and counted using scintillation counter.

Result Analysis and Determination of 50% Inhibitory Concentration (IC$_{50}$):

The IC$_{50}$ value was calculated by using (Prism 4) software, and 50% inhibitory concentrations were obtained.

TABLE 1

Representative compounds and activities:

| Examples | Name | IC$_{50}$ (nM) |
|---|---|---|
| 10 | 7-{5-[4-(2-methoxyethoxy) phenyl]-2-[1,3,4]oxdiazolyl]-2-amino-1,2,3,4-tetrahydro-naphthalen-2-yl-methanol | 31.7 |
| 11 | 7-[5-(3-trifluoromethyl-4-isopropoxyphenyl)-2-[1,3,4] oxdiazolyl]-2-amino-1,2,3,4-tetrahydro-naphthalen-2-yl-methanol | 0.4 |
| 12 | 6-[5-(3-nitro-4-pyridyl)-3-1,2,4-oxdiazolyl]-2-amino-1,2,3,4-tetrahydro-naphthalen-2-yl-methanol | 620 |
| 15 | 7-[5-(4-methoxy-3-methyl phenyl)-2-1,3,4-oxdiazolyl]-2-amino-1,2,3,4-tetrahydro-naphthalen-2-yl-methanol | 16 |
| 16 | 7-[5-(4-isopropoxyphenyl)-2-1,3,4-oxydiazolyl]-2-amino-1,2,3,4-tetrahydro-naphthalen-2-yl-methanol | 46 |
| 17 | 7-{5-[4-(2-methoxyethoxy)-3-trifluoromethyl phenyl]-2-1,3,4-oxdiazolyl}-2-amino-1,2,3,4-tetrahydro-naphthalen-2-yl-methanol | 10.2 |
| 18 | 7-{5-[4-(2-methoxyethoxy)-3-methyl phenyl]-2-1,3,4-oxdiazolyl}-2-amino-1,2,3,4-tetrahydro-naphthalen-2-yl-methanol | 41.1 |

TABLE 1-continued

Representative compounds and activities:

| Examples | Name | IC$_{50}$ (nM) |
|---|---|---|
| 19 | 7-[5-(6-isopropoxy-3-pyridyl)-2-1,3,4-oxdiazolyl]-2-amino-1,2,3,4-tetrahydro-naphthalen-2-yl-methanol | 61.2 |
| 20 | 7-[5-(3,4-diethoxyphenyl)-2-[1,3,4]-oxdiazolyl]-2-amino-1,2,3,4-tetrahydro-naphthalen-2-yl-methanol | 179 |
| 21 | 2-(7-benzylamino-5,6,7,8-tetrahydro-7-naphthalenemethanol)-5-(3-methyl-4-isopropoxy)-1,3,4-oxdiazole | 179 |
| 22 | 2-(7-amino-5,6,7,8-tetrahydro-7-naphthalenemethanol)-5-(3-methyl-4-isopropoxy)-1,3,4-oxdiazole | 3.0 |
| 23 | 7-[5-(3-methyl-4-isopropoxyphenyl)-2-1,3,4-oxdiazolyl]-2-Ethylamino-1,2,3,4-tetrahydro-naphthalen-2-yl-methanol | 37.6 |
| 24 | 7-[5-(3-methyl-4-isopropoxyphenyl)-2-1,3,4-oxdiazolyl]-2-Dimethylamino-1,2,3,4-tetrahydro-naphthalen-2-yl-methanol | 46 |
| 25 | N-{2-hydroxymethyl-7-[5-(3-methyl-4-isopropoxyphenyl)-2-1,3,4-oxdiazolyl]-1,2,3,4-tetrahydro-naphthalen-2-yl} acetamide | 45.5 |
| 26 | N-{2-hydroxymethyl-7-[5-(3-methyl-4-isopropoxyphenyl)-2-1,3,4-oxdiazolyl]-1,2,3,4-tetrahydro-naphthalen-2-yl} methanesulfonamide | 86.0 |
| 27 | 7-[3-(3-methyl-4-isopropoxyphenyl)-5-1,2,4-oxdiazolyl]-2-amino-1,2,3,4-tetrahydro-naphthalen-2-yl-methanol | 1.20 |
| 28 | 6-[3-(3-methyl-4-isopropoxyphenyl)-5-1,2,4-oxdiazolyl]-2-amino-1,2,3,4-tetrahydro-naphthalen-2-yl-methanol | 473 |
| 29 | 7-[5-(3-methyl-4-isopropoxyphenyl)-3-1,2,4-oxdiazolyl]-2-amino-1,2,3,4-tetrahydro-naphthalen-2-yl-methanol | 0.40 |
| 30 | 6-[5-(3-methyl-4-isopropoxyphenyl)-3-1,2,4-oxdiazolyl]-2-amino-1,2,3,4-tetrahydro-naphthalen-2-yl-methanol | 749 |
| 31 | 7-[4-(3-methyl-4-isopropoxyphenyl)-1-1,2,3-triazolyl]-2-amino-1,2,3,4-tetrahydro-naphthalen-2-yl-methanol | 5.0 |
| 32 | 6-[4-(3-methyl-4-isopropoxyphenyl)-1-1,2,3-triazolyl]-2-amino-1,2,3,4-tetrahydro-naphthalen-2-yl-methanol | 125 |

2. S1P1 β-Arrestin Assay 2.1 Experimental Materials: Path hunter express CHO-K1 EDG1 β-arrestin GPCR Assay was purchased from DiscoveRx, containing CHO-EDG-1 cells, buffers, substrate-1, substrate-2, cell culture fluid, 96-well cell culture plate.

2.2 Equipment
1) Super-clean bench for cell culture
2) Evision 2104 cell plate counter
3) 37° C. incubator 2.3 Test Method
1) The test compounds were dissolved in DMSO and prepared as a concentration of 20 mM.
2) The concentrations of the test compounds were detected ranging from 0.3 mM to 20 µM.
3) Control group: 0.045 nM-3 µM S1P purchased from Tocris company; while the binding buffer was used as the negative control.

4) Assay procedures: OCC culture solution was preheated in water tank at 37° C. Cells were taken out from liquor nitrogen tank, left on the dry-ice, and dissolved in water tank at 37° C. 0.5 ml OCC culture solution was added and blended slowly. The cells were diluted in 11.5 mL OCC culture solution, and 100 µL cell suspension (containing 8333 cells) was added to each well of the 96-well plate. The 96-well plate was incubated for 8 hours under 5% CO$_2$ at 37° C., and 10 µL test compound dissolved in DMSO was added in; 10 µL DMSO was used as negative control. After the plate was incubated for 90 min at 37° C., 55 µL detection solution was added to each well. Then the results were read out by EnVision after the cell plate was incubated for 90 min at room temperature.

2.4 Result Analysis and Determination of Concentration, for 50% of Maximal Effect (EC$_{50}$):

The EC$_{50}$ Value was Calculated by Using Prism 4 Software

| Examples | Name | EC$_{50}$ (nM) |
|---|---|---|
| 10 | 7-{5-[4-(2-methoxyethoxy) phenyl]-2-[1,3,4]oxdiazolyl]-2-amino-1,2,3,4-tetrahydro-naphthalen-2-yl-methanol | 77 |
| 11 | 7-[5-(3-trifluoromethyl-4-iso propoxyphenyl)-2-[1,3,4] oxdiazolyl]-2-amino-1,2,3,4-tetrahydro-naphthalen-2-yl-methanol | 3.1 |
| 15 | 7-[5-(4-methoxy-3-methyl phenyl)-2-1,3,4-oxdiazolyl]-2-amino-1,2,3,4-tetrahydro-naphthalen-2-yl-methanol | 27 |
| 22 | 2-(7-amino-5,6,7,8-tetrahydro-7-naphthalenemethanol)-5-(3-methyl-4-isopropoxy)-1,3,4-oxdiazole | 8 |
| 24 | 7-[5-(3-methyl-4-isopropoxyphenyl)-2-1,3,4-oxdiazolyl]-2-dimethylamino-1,2,3,4-tetrahydro-naphthalen-2-yl-methanol | 354 |
| 27 | 7-[3-(3-methyl-4-isopropoxyphenyl)-5-1,2,4-oxdiazolyl]-2-amino-1,2,3,4-tetrahydro-naphthalen-2-yl-methanol | 20 |
| 29 | 7-[5-(3-methyl-4-isopropoxyphenyl)-3-1,2,4-oxdiazolyl]-2-amino-1,2,3,4-tetrahydro-naphthalen-2-yl-methanol | 9.9 |
| 31 | 7-[4-(3-methyl-4-isopropoxyphenyl)-1-1,2,3-triazolyl]-2-amino-1,2,3,4-tetrahydro-naphthalen-2-yl-methanol | 14.3 |

3. Effects of the Compounds in Example-21 and Example-22 on Peripheral Blood Lymphocyte in Mice 3.1 Experimental Materials:

1) 15% EDTA, PBS, EP tubes, 15 ml centrifuge tube, capillary tube, pipette tip were all purchased from Shanghai biological technology co., Ltd. Hemocyte analysis reagents were purchased from Shanghai Sysmex Company.

2) 35 Balb/c mice (female, 20-22 g), supplied by laboratory animal center of Jilin University.

3) Automated Hematology Analyzer (pocH-100 iV Diff) was purchased from Sysmex Company, Kobe, Japan.

3.2 Assay Method:

1) The stock solutions of the compounds obtained in Example-21 and Example-22 were prepared with normal saline, and the concentrations are 2 mg/ml and 20 mg/ml, respectively.

2) The mice were divided into 5 groups, i.e., control group, low-dose experimental group, and high-dose experimental group. They were weighed and labeled well.

3) Before administration, supraorbital venous blood was collected with 20 µl/mouse which was added to anticoagulant tube containing EDTA, and nosed thoroughly. The numbers of lymphocytes were analyzed by pocH-100.

4) The control group was given normal saline: low-dose experimental groups were given the compounds obtained in Example-21 and Example-22 (5 mg/kg/d), high-dose experimental groups were given the compounds obtained in Example-21 and Example-22 (30 mg/kg/d), with liquid amount of 500 µl/mouse, by intragastric administration. Administration was performed for continuous four days, once a day. After 3.5 hours of the first and fourth administration, blood was collected respectively, and changes in the numbers of lymphocytes were analyzed by pocH-100.

3.3 Conclusions:

With the compounds in Example-21 and Example-22 were given continuously for four days, the biological markers in vivo: the numbers of peripheral blood lymphocyte in mice were reduced by 92% and 78%, respectively, compared to pre-administration. While FTY720 generally causes the number of peripheral blood lymphocytes decreased by 70-80%. The behavior and weight of mice showed no differences between pre- and post-administration. The dose up to 30 mg/kg/d exhibited no toxicity effects.

It demonstrated that the above experiment can be $S1P_1$ in vivo biological marker assay.

4. Experimental Autoimmune Multiple Sclerosis 4.1 Materials

1) SJL/J mice (8-9 weeks, female) were purchased from JAX Lab.

2) PLP139-151 (HSLGKWLGHPDKF amide) was ordered from Biosource Internaional Company (QCB).

3) Incomplete Freund's adjuvant (IFA) was purchased from Difco Company.

4) *Mycobacterium tuberculosis* H37 was purchased from Difco Company.

5) *Escherichia coli* pertussis toxin was purchased from Calbiochem Company.

6) 1.0 ml insulin injection syringes, 10 ml injectors, tee connectors.

4.2 Immunization of Mice

1) Preparation of Complete Freund's adjuvant (CFA): *Mycobacterium tuberculosis* H37 was added to incomplete freund's adjuvant (IFA) to produce complete freund's adjuvant (CFA) containing 8.0 mg/ml *mycobacterium tuberculosis*.

2) PLP polypeptides were dissolved in PBS solution to prepare 10 mg/ml, and the working concentration is 2.0 mg/ml.

3) PLP polypeptide antigens were mixed with CFA.

4) Immunizing mice: each mouse was inoculated with 100 µg PLP139-151 and 0.4 mg *mycobacterium tuberculosis*.

5) At the day of immunization and the next day, each mouse was intraperitoneally injected with 100 ng pertussis toxin.

4.3 Assay Method:

1) The stock solutions of the compounds obtained in Example-21 and Example-22 were prepared with 20% 2-hydroxypropyl-β-cyclodextrin into a concentration of 2 mg/ml and 20 mg/ml, respectively.

2) The mice were divided into 5 groups, i.e., control group, low-dose experimental group, and high-dose experimental group. They were weighed and labeled well.

3) The Control group was treated with 20% 2-hydroxypropyl-β-cyclodextrin; low-dose experimental group was given the compounds obtained in Example-21 and Example-22 (5 mg/kg/d); high-dose experimental group was given the compounds obtained in Example-21 and Example-22 (30 mg/kg/d), with liquid amount: of 500 µl/mouse, intragastric administration. Administration was performed at the next day after immunization and continuously for 30 days, once a day. The changes of the animals' diseases were recorded every day.

4.3 The Standard for Evaluation Scores of the Diseases: 0, normal; 1, tail paralysis; 2, hind limbs weakness; 3, hind limbs paralysis; 4, fore and hind limbs paralysis; 5, impending death or death.

4.4 Experiment Results: the compounds obtained in Example-21 and Example-22 showed remarkable inhibitory effects on the induction and development of autoimmune multiple sclerosis.

5. Experimental Rheumatoid Arthritis 5.1 Material 1) 10 mM acetic acid, 0.2 µm filter;

2) Incomplete Freund's Adjuvant (IFA), *mycobacterium tuberculosis* (inactivated strain H37Ra), were purchased from Difco Company.

3) DBA/1JLacJ mice (Jackson Lab)

4) Bovine collagen type II was purchased from Chondrex Company.

5.2 Preparation of Antigens

1) Bovine collagen type II was dissolved in 10 mM acetic acid, and stayed overnight at 4° C.

2) The heat-inactivated *mycobacterinm tuberculosis* was ground by mortar and pestle, and was prepared into complete Freund's adjuvant (CFA) at final concentration of 4 mg/ml.

5.3 Experiment Method:

1) The stock solutions of the compounds obtained in Example-21 and Example-22 were prepared with 20% 2-hydroxypropyl-β-cyclodextrin into a concentration of 2 mg/ml and 20 mg/ml, respectively.

2) The mice were divided into 5 groups, i.e., control group, low-dose experimental group, and high-dose experimental group. They were weighed and labeled well.

3) The Control group was treated with 20% 2-hydroxypropyl-β-cyclodextrin; low-dose experimental group was given the compounds obtained in Example-21 and Example-22 (5 mg/kg/d); high-dose experimental group was given the compounds obtained in Example-21 and Example-22 (30 mg/kg/d), with liquid amount of 500 µl/mouse, intragastric administration. Administration was performed at the next day after immunization and continuously for 30 days, once a day. The changes of the animals' diseases were recorded every day.

5.4 The Development and Evaluation on Arthritis of the Immunized Mice: each mouse was injected with the mixture of 100 μg *mycobacterium tuberculosis* and 100 μg bovine collagen type II.

5.5 Evaluation on the Development of Arthritis: arthritis was usually occurred after 3-5 weeks, and reached peak in the 6th week.

5.6 Experiment Results: the compounds obtained in Example-21 and Example-22 showed remarkable inhibitory effects on induction and development of experimental rheumatoid arthritis.

What is claimed is:

1. A heterocyclic amino-methanol compound represented by the formula:

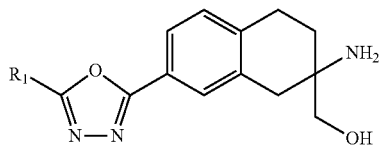

wherein
$R_1$ is

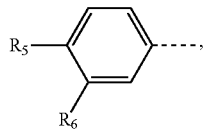

where $R_5$ is selected from the group consisting of alkyl, alkoxy and $R_7OCH_2CH_2O$; $R_6$ is selected from the group consisting of H, alkyl, ethoxy and fluoroalkyl; and $R_7$ is alkyl;

or a salt thereof.

2. The heterocyclic amino-methanol compound of claim 1, which is selected from the group consisting of:
   7-{5-[4-(2-methoxyethoxy)phenyl]-2-[1,3,4]oxadiazolyl]-2-amino-1,2,3,4-tetrahydronaphthalen-2-yl-methanol,
   7-[5-(3-trifluoromethyl-4-isopropoxyphenyl)-2-[1,3,4]oxadiazolyl]-2-amino-1,2,3,4-tetrahydronaphthalen-2-yl-methanol,
   7-[5-(4-methoxy-3-methylphenyl)-2-[1,3,4]oxadiazolyl]-2-amino-1,2,3,4-tetrahydronaphthalen-2-yl-methanol,
   7-[5-(4-isopropoxyphenyl)-2-[1,3,4]oxadiazolyl]-2-amino-1,2,3,4-tetrahydronaphthalen-2-yl-methanol,
   7-{5-[4-(2-methoxyethoxy)-3-trifluoromethyl phenyl]-2-[1,3,4]oxadiazolyl}-2-amino-1,2,3,4-tetrahydronaphthalen-2-yl-methanol,
   7-{5-[4-(2-methoxyethoxy)-3-methyl phenyl]-2-[1,3,4]oxadiazolyl}-2-amino-1,2,3,4-tetrahydronaphthalen-2-yl-methanol,
   7-[5-(3,4-diethoxyphenyl)-2-[1,3,4]oxadiazolyl]-2-amino-1,2,3,4-tetrahydronaphthalen-2-yl-methanol,
and physiologically acceptable salts thereof.

3. A compound which is 7-[5-(3-trifluoromethyl-4-isopropoxyphenyl)-2-[1,3,4]oxadiazolyl]-2-amino-1,2,3,4-tetrahydronaphthalen-2-yl-methanol, or a physiologically acceptable salt thereof.

4. A compound which is 7-[5-(3,4-diethoxyphenyl)-2-[1,3,4]oxadiazolyl]-2-amino-1,2,3,4-tetrahydronaphthalen-2-yl-methanol, or a physiologically acceptable salt thereof.

* * * * *